US005786324A

United States Patent [19]
Gray et al.

[11] Patent Number: 5,786,324
[45] Date of Patent: Jul. 28, 1998

[54] SYNTHETIC PEPTIDES WITH BACTERICIDAL ACTIVITY AND ENDOTOXIN NEUTRALIZING ACTIVITY FOR GRAM NEGATIVE BACTERIA AND METHODS FOR THEIR USE

[75] Inventors: Beulah Gray, St. Paul; Judith R. Haseman, Eagan; Kevin Mayo, Minnetonka, all of Minn.

[73] Assignee: Regents of the University of Minnesota, Minneapolis, Minn.

[21] Appl. No.: 218,026

[22] Filed: Mar. 24, 1994

[51] Int. Cl.$^6$ .................... A61K 38/12; A61K 38/04
[52] U.S. Cl. .................... 514/9; 514/12; 514/13; 514/14; 514/15; 514/21; 435/69.7
[58] Field of Search .................... 514/9, 12, 13, 514/14, 15, 21; 435/69.7

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott | 514/12 |
| 5,198,541 | 3/1993 | Elsbach et al. | 435/69.1 |
| 5,334,584 | 8/1994 | Scott et al. | 514/12 |
| 5,348,942 | 9/1994 | Little et al. | 514/12 |

FOREIGN PATENT DOCUMENTS

| | | |
|---|---|---|
| WO 89/01486 | 2/1989 | WIPO . |
| WO 90/09183 | 8/1990 | WIPO . |
| WO 92/09621 | 6/1992 | WIPO . |
| WO 93/05797 | 4/1993 | WIPO . |
| WO 93/23434 | 11/1993 | WIPO . |
| WO 94/17819 | 8/1994 | WIPO . |
| WO 94/18323 | 8/1994 | WIPO . |
| WO 94/20531 | 9/1994 | WIPO . |
| WO 94/25476 | 11/1994 | WIPO . |
| WO 95/00641 | 1/1995 | WIPO . |
| WO 95/01428 | 1/1995 | WIPO . |
| WO 95/02414 | 1/1995 | WIPO . |

OTHER PUBLICATIONS

Hoess et al., "Crystal Structure of an Endotoxin–Neutralizing Protein from the Horseshoe Crab, Limulus Anti–LPS Factor, at 1.5 A Resolution", *EMBO Journal*, 12:3351–3356 (1993).
Johnston, "Molecular Science Sets Its Sights on Septic Shock", *J. NIH Res*, 3:61–65 (1991).
Little et al., "Functional Domains of Recombinant Bactericidal/Permeability Increasing Protein (rBPI$_{23}$)", *J. Biol. Chem.*, 269:1865–1872 (1994).
Pereira et al., "Synthetic Bactericidal Peptide Based on CAP37: A 37–kDa Human Neutrophil Granule–associated Cationic Antimicrobial Protein Chemotactic for Monocytes", *Proc. Natl. Acad. Sci. USA*, 90:4733–4737 (1993).
Shafer et al., "Synthetic Peptides of Human Lysosomal Cathepsin G with Potent Antipseudomonal Activity", *Infection and Immunity*, 61:1900–1908 (1993).
Bangalore et al., "Identification of the Primary Antimicrobial Domains in Human Neutrophil Cathepsin G", *J. Biol. Chem.*, 265:13584–13588 (1990).
Bottone et al., "Association of *Pseudomonas cepacia* with Chronic Granulomatous Disease", *J. Clin. Micro.*, 1:425–428 (1975).
Brown et al., "Chemical Synthesis and Cloning of a Tyrosine tRNA Gene", *Methods in Enzymology*, 68:109–151 (1979).
Campanelli et al., "Azurocidin and a Homologous Serine Protease from Neutrophils", *J. Clin. Invest.*, 85:904–915 (1990).
Capone, "Screening Recombinant Baculovirus Placques In Situ with Antibody Probes", *Gene Anal. Techn.*, 6:62–66 (1989).
Casey et al., "*Neisseria gonorrhoeae* Survive Intraleukocytic Oxygen—Independent Antimicrobial Capacities of Anaerobic and Aerobic Granulocytes in the Presence of Pyocin Lethal for Extracellular Gonococci", *Infect. Immun.*, 52:384–389 (1986).
Cody et al., "Protective Anti–Lipopolysaccharide Monoclonal Antibodies Inhibit Tumor Necrosis Factor Production", *J. Surg. Res.*, 52:314–319 (1992).
Dugas et al., "Chemical Synthesis of Proteins", *Bioorganic Chemistry*, Springer–Verlag, NY at pp. 54–92 (1981).
Dunn et al., "Efficacy of Type–Specific and Cross–Reactive Murine Monoclonal Antibodies Directed Against Endotoxin During Experimental Sepsis", *Surgery*, 98:283–290 (1985).
Elsbach et al., "Bactericidal/permeability Increasing Protein and Host Defense Against Gram–negative Bacterial and Endotoxin", *Current Opinion in Immunology*, 5:103–107 (1993).
Farley et al., "Lipopolysaccharide Structure Determines Ionic and Hydrophobic Binding of a Cationic Antimicrobial Neutrophil Granule Protein", *Infect. Immun.*, 56:1589–1592 (1988).
Gabay et al., "Antibiotic Proteins of Human Polymorphonuclear Leukocytes", *Proc. Natl. Acad. Sci.*, 86:5610–5614 (1989).
Gallin, "Recent Advances in Chronic Granulomatous Disease", *Ann. Int. Med.*, 99:657–674 (1983).
Gazzano–Santoro et al., "High–Affinity Binding of the Bactericidal/Permeability—Increasing Protein and a Recombinant Amino–Terminal Fragment to the Lipid A Region of Lipopolysaccharide", *Infect. Immun.*, 60:4754–4761 (1992).
Gray et al., "Cloning of the cDNA of a Human Neutrophil Bactericidal Protein", *J. Biol. Chem.*, 264:9505–9509 (1989).
Hancock, "Alterations in Outer Membrane Permeability", *Ann. Rev. Microbiol.*, 38:237–264 (1984).

(List continued on next page.)

*Primary Examiner*—Charles L. Patterson, Jr.
*Attorney, Agent, or Firm*—Merchant, Gould, Smith, Edell, Welter & Schmidt

[57] ABSTRACT

The invention provides biologically active peptides derived from or corresponding to regions of a bactericidal permeability increasing factor (B/PI). The peptides are about 10 to 100 amino acids long and have bactericidal and/or endotoxin neutralizing activity. The peptides can be prepared by automated DNA synthesis or by recombinant DNA methods. The peptides are useful in methods to treat and prevent bacterial infection in the body and on surfaces. The peptides are also useful to treat endotoxin shock.

27 Claims, 10 Drawing Sheets

OTHER PUBLICATIONS

Hartree, "Determination of Protein: A Modification of the Lowry Method that Gives a Linear Photometric Response", *Anal. Biochem.*, 48:422–427 (1972).

Heumann et al., "Competition between Bactericidal/Permeability—Increasing Protein and Lipopolysaccharide–Binding Protein for Lipopolysaccharide Binding to Monocytes" *J. Infect. Dis.*, 167:1351–1357 (1993).

Holmes et al., "Fatal Granulomatous Disease of Childhood", *Lancet*, 1:1225–1228 (1966).

Holmes et al., "Studies of the metabolic Activity of Leukocytes from Patients with a Genetic Abnormality of Phagocytic Function", *J. Clin. Invest.*, 46:1422–1432 (1967).

Holmes, "Metabolic Stimulation and Bactericidal Function of Polymorphonuclear Leukocytes", *Reticulo. Soc.*, 22:87–88 (1978).

Homma, "A New Antigenic Schema and Live–cell Slide–agglutination Procedure for the Infrasubspecific. Serologic Classification of *Pseudomonas aeruginosa*", *Jpn. J. Exp. Med.*, 46:329–336 (1976).

Hovde et al., "Physiological Effects of a Bactericidal Protein from Human Polymorphonuclear Leukocytes on *Pseudomonas aeruginosa*", *Infect. Immun.*, 52:90–95 (1986).

Hovde et al., "Characterization of a Protein from Normal Human Polymorphonuclear Leukocytes with Bactericidal Activity Against *Pseudomonas aeruginosa*", *Infect Immun.*, 54:142–148 (1986).

Johnston et al., "Chronic Granulomatous Disease", *Ped. Clin. of N. Amer.*, 24:365–376 (1977).

Kambic et al., "Biomaterials in Artificial Organs", *Chem. & Eng. News* at pp. 31–48 (Apr. 14, 1986).

Kelly et al., "Role of Bactericidal Permeability—Increasing Protein in the Treatment of Gram–Negative Pneumonia", *Surgery*, 114:140–146 (1993).

Kyte et al., "A Simple Method for Displaying the Hydropathic Character of a Protein", *J. Mol. Biol.*, 157:105–132 (1982).

Larrick et al., "Polymerase Chain Reaction Using Mixed Primers: Cloning of Human Monoclonal Antibody Variable Region Genes from Single Hybridoma Cells", *Bio/Tech*, 7:934–938 (1989).

Lehrer et al, "Defensins: Antimicrobial and Cytotixic Peptides of mammalian Cells", *Ann. Rev. of Immunol.*, 11:105–128 (1993).

Luckow et al. "Trends in the Development of Baculovirus Expression Vectors", *Biotech*, 6:47–55 (1988).

Mandell, "Bactericidal Activity of Aerobic and Anaerobic Polymorphonuclear Neutrophils", *Infect. Immun.*, 9:337–341 (1974).

Mannion et al., "Separation of Sublethal and Lethal Effects of the Bactericidal/Permeability Increasing Protein on *Escherichia coli*", *J. Clin. Invest.*, 85:853–860 (1990).

Marra et al., "Bactericidal/Permeability—Increasing Protein has Endotoxin–Neutralizing Activity", *J. Immunol.*, 144:662–666 (1990).

Marra et al., "The Role of Bactericidal/Permeability—Increasing Protein as a Natural Inhibitor of Bacterial Endotoxin", *J. Immunol.*, 148:532–537 (1992).

Mossman et al., "Rapid Colorimetric Assay for Cellular Growth and Survival: Application to Proliferation and Cytotoxicity Assays", *Immunological Methods*, 65:55–63 (1983).

Okamura et al., "Outer Membrane Mutants of *Salmonella typhimurium* LT2 Have Lipopolysaccharide–Dependent Resistance to the Bactericidal Activity of Anaerobic Human Neutrophlis", *Infect. Immun.*, 36:1086–1095 (1992).

Ooi et al., "A 25–kDa $NH_2$–terminal Fragment Carries all the Antibacterial Activities of the Human Neutrophil 60–kDa Bactericidal/Permeability—Increasing Protein", *J. Biol. Chem.*, 262:14891–14894 (1987).

Ooi et al., "Endotoxin–neutralizing Properties of the 25 kD N–Terminal Fragment and a Newly Isolated 30 kD C–Terminal Fragment of the 55–60 kD Bactericidal/Permeability—Increasing Protein of Human Neutrophils", *J. Exp. Med.*, 174:649–654 (1991).

Quie et al., "In Vitro Bactericidal Capacity of Human Polymorphonuclear Leukocytes: Diminished Activity in Chronic Granulomatous Disease of Childhood", *J. Clin. Invest.*, 46:668–679 (1967).

Rest, "Killing of *Neisseria gonorrhoeae* by Human Polymorphonuclear Neutrophil Granule Extracts", *Infect. Immun.*, 25:574–579 (1979).

Rest et al., "Interactions of *Neisseria gonorrhoeae* with Human Neutrophils: Effects of Serum and Gonococcal Opacity on Phagocyte Killing and Chemiluminescence", *Infect. Immun.*, 36:737–744 (1982).

Rustici et al., "Molecular Mapping and Detoxification of the Lipid A Binding Site by Synthetic Peptides", *Science*, 259:361–365 (1993).

Shafer et al., "Lipid A and Resistance of *Salmonella typhimurium* to Antimicrobial Granule Proteins of Human Neutrophil Granulocytes", *Infect. Immun.*, 43:834–838 (1984).

Shafer et al., "Cationic Antimicrobial Proteins Isolated from Human Neutrophil Granulocytes in the Presence of Diisopropyl Fluorophosphate", *Infect. Immun.*, 45:29–35 (1984).

Shinefield et al., "Preliminary Observations on Artificial Colonization of Newborns", *Amer. J. Dis. Chil.*, 105:146–154 (1963).

Siefferman et al., "*Pseudomonas aeruginosa* Variants Isolated from Patients with Cystic Fibrosis are Killed by a Bactericidal Protein from Human Polymorphonuclear Leukocytes", *Infect. Immun.*, 59:2152–2157 (1991).

Spitznagel, "Antibiotic Proteins of Human Neutrophils", *J. Clin. Invest.*, 86:1381–1386 (1990).

Wang et al., "Direct Double–Stranded DNA Sequencing with Baculovirus Genomes", *J. Virol. Meth.*, 31:113–118 (1991).

Wasiluk et al., "Comparison of Granule Proteins from Human Polymorphonuclear Leukocytes Which are Bactericidal Toward *Pseudomonas aeruginosa*", *Infect. Immun.*, 59:4193–4200 (1991).

Weiss et al., "Purification and Characterization of a Potent Bactericidal and Membrane Active Protein from the Granules of Human Polymorphonuclear Leukocytes", *J. Biol. Chem.*, 253:2664–2672 (1978).

Weiss et al., "Killing of Gram–Negative Bacteria by Polymorphonuclear Leukocytes", *J. Clin. Invest.*, 69:959–970 (1982).

Weiss et al., "Environmental Modulation of Lipopolysaccharide Chain Length Alters the Sensitivity of *Escherichia coli* to the Neutrophil Bactericidal/Permeability—Increasing Protein", *Infect. Immun.*, 51:594–599 (1986).

Weiss et al., "Human Bactericidal/Permeability—Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.*, 90:1122–1130 (1992).

FIG. 4

```
ATG AGA GAG AAC ATG GCC AGG GGC CCT TGC AAC GCG CCG AGA TGG GTG   48
Met Arg Glu Asn Met Ala Arg Gly Pro Cys Asn Ala Pro Arg Trp Val
 1               5                  10                  15

TCC CTG ATG GTG CTC GTC GCC ATA GGC ACC GCC GTG ACA GCG GCC GTC   96
Ser Leu Met Val Leu Val Ala Ile Gly Thr Ala Val Thr Ala Ala Val
            20                  25                  30

AAC CCT GGC GTC GTG GTC AGG ATC TCC CAG AAG GGC CTG GAC TAC GCC  144
Asn Pro Gly Val Val Val Arg Ile Ser Gln Lys Gly Leu Asp Tyr Ala
        35                  40                  45

AGC CAG CAG GGG ACG GCC GCT CTG CAG AAG GAG CTG AAG AGG ATC AAG  192
Ser Gln Gln Gly Thr Ala Ala Leu Gln Lys Glu Leu Lys Arg Ile Lys
    50                  55                  60

ATT CCT GAC TAC TCA GAC AGC TTT AAG ATC AAG CAT CTT GGG AAG GGG  240
Ile Pro Asp Tyr Ser Asp Ser Phe Lys Ile Lys His Leu Gly Lys Gly
65                  70                  75                  80

CAT TAT AGC TTC TAC AGC ATG GAC ATC CGT GAA TTC CAG CTT CCC AGT  288
His Tyr Ser Phe Tyr Ser Met Asp Ile Arg Glu Phe Gln Leu Pro Ser
                85                  90                  95

TCC CAG ATA AGC ATG GTG CCC AAT GTG GGC CTT AAG TTC TCC ATC AGC  336
Ser Gln Ile Ser Met Val Pro Asn Val Gly Leu Lys Phe Ser Ile Ser
            100                 105                 110

AAC GCC AAT ATC AAG ATC AGC GGG AAA TGG AAG GCA CAA AAG AGA TTC  384
Asn Ala Asn Ile Lys Ile Ser Gly Lys Trp Lys Ala Gln Lys Arg Phe
        115                 120                 125

TTA AAA ATG AGC GGC AAT TTT GAC CTG AGC ATA GAA GGC ATG TCC ATT  432
Leu Lys Met Ser Gly Asn Phe Asp Leu Ser Ile Glu Gly Met Ser Ile
    130                 135                 140

TCG GCT GAT CTG AAG CTG GGC AGT AAC CCC ACG TCA GGC AAG CCC ACC  480
Ser Ala Asp Leu Lys Leu Gly Ser Asn Pro Thr Ser Gly Lys Pro Thr
145                 150                 155                 160

ATC ACC TGC TCC AGC TGC AGC AGC CAC ATC AAC AGT GTC CAC GTG CAC  528
Ile Thr Cys Ser Ser Cys Ser Ser His Ile Asn Ser Val His Val His
                165                 170                 175
```

FIG. 4A

```
ATC TCA AAG AGC AAA GTC GGG TGG CTG ATC CAA CTC TTC CAC AAA AAA  576
Ile Ser Lys Ser Lys Val Gly Trp Leu Ile Gln Leu Phe His Lys Lys

ATT GAG TCT GCG CTT CGA AAC AAG ATG AAC AGC CAG GTC TGC GAG AAA  624
Ile Glu Ser Ala Leu Arg Asn Lys Met Asn Ser Gln Val Cys Glu Lys
            195                 200                 205

GTG ACC AAT TCT GTA TCC TCC AAG CTG CAA CCT TAT TTC CAG ACT CTG  672
Val Thr Asn Ser Val Ser Ser Lys Leu Gln Pro Tyr Phe Gln Thr Leu
    210                 215                 220

CCA GTA ATG ACC AAA ATA GAT TCT GTG GCT GGA ATC AAC TAT GGT CTG  720
Pro Val Met Thr Lys Ile Asp Ser Val Ala Gly Ile Asn Tyr Gly Leu
225                 230                 235                 240

GTG GCA CCT CCA GCA ACC ACG GCT GAG ACC CTG GAT GTA CAG ATG AAG  768
Val Ala Pro Pro Ala Thr Thr Ala Glu Thr Leu Asp Val Gln Met Lys
                245                 250                 255

GGG GAG TTT TAC AGT GAG AAC CAC CAC AAT CCA CCT CCC TTT GCT CCA  816
Gly Glu Phe Tyr Ser Glu Asn His His Asn Pro Pro Pro Phe Ala Pro
            260                 265                 270

CCA GTG ATG GAG TTT CCC GCT GCC CAT GAC CGC ATG GTA TAC CTG GGC  864
Pro Val Met Glu Phe Pro Ala Ala His Asp Arg Met Val Tyr Leu Gly
        275                 280                 285

CTC TCA GAC TAC TTC TTC AAC ACA GCC GGG CTT GTA                  900
Leu Ser Asp Tyr Phe Phe Asn Thr Ala Gly Leu Val
    290                 295                 300
```

FIG. 8

```
ATG AGA GAG AAC ATG GCC AGG GGC CCT TGC AAC GCG CCG AGA TGG GTG   48
Met Arg Glu Asn Met Ala Arg Gly Pro Cys Asn Ala Pro Arg Trp Val
 1               5                  10                  15

TCC CTG ATG GTG CTC GTC GCC ATA GGC ACC GCC GTG ACA GCG GCC GTC   96
Ser Leu Met Val Leu Val Ala Ile Gly Thr Ala Val Thr Ala Ala Val
             20                  25                  30

AAC CCT GGC GTC GTG GTC AGG ATC TCC CAG AAG GGC CTG GAC TAC GCC  144
Asn Pro Gly Val Val Val Arg Ile Ser Gln Lys Gly Leu Asp Tyr Ala
         35                  40                  45

AGC CAG CAG GGG ACG GCC GCT CTG CAG AAG GAG CTG AAG AGG ATC AAG  192
Ser Gln Gln Gly Thr Ala Ala Leu Gln Lys Glu Leu Lys Arg Ile Lys
 50                  55                  60

ATT CCT GAC TAC TCA GAC AGC TTT AAG ATC AAG CAT CTT GGG AAG GGG  240
Ile Pro Asp Tyr Ser Asp Ser Phe Lys Ile Lys His Leu Gly Lys Gly
 65                  70                  75                  80

CAT TAT AGC TTC TAC AGC ATG GAC ATC CGT GAA TTC CAG CTT CCC AGT  288
His Tyr Ser Phe Tyr Ser Met Asp Ile Arg Glu Phe Gln Leu Pro Ser
             85                  90                  95

TCC CAG ATA AGC ATG GTG CCC AAT GTG GGC CTT AAG TTC TCC ATC AGC  336
Ser Gln Ile Ser Met Val Pro Asn Val Gly Leu Lys Phe Ser Ile Ser
         100                 105                 110

AAC GCC AAT ATC AAG ATC AGC GGG AAA TGG AAG GCA CAA AAG AGA TTC  384
Asn Ala Asn Ile Lys Ile Ser Gly Lys Trp Lys Ala Gln Lys Arg Phe
         115                 120                 125

TTA AAA ATG AGC GGC AAT TTT GAC CTG AGC ATA GAA GGC ATG TCC ATT  432
Leu Lys Met Ser Gly Asn Phe Asp Leu Ser Ile Glu Gly Met Ser Ile
 130                 135                 140

TCG GCT GAT CTG AAG CTG GGC AGT AAC CCC ACG TCA GGC AAG CCC ACC  480
Ser Ala Asp Leu Lys Leu Gly Ser Asn Pro Thr Ser Gly Lys Pro Thr
145                 150                 155                 160

ATC ACC TGC TCC AGC TGC AGC AGC CAC ATC AAC AGT GTC CAC GTG CAC  528
Ile Thr Cys Ser Ser Cys Ser Ser His Ile Asn Ser Val His Val His
             165                 170                 175
```

FIG. 8A

```
ATC TCA AAG AGC AAA GTC GGG TGG CTG ATC CAA CTC TTC CAC AAA AAA   576
Ile Ser Lys Ser Lys Val Gly Trp Leu Ile Gln Leu Phe His Lys Lys
            180                 185                 190

ATT GAG TCT GCG CTT CGA AAC AAG ATG AAC AGC CAG GTC TGC GAG AAA   624
Ile Glu Ser Ala Leu Arg Asn Lys Met Asn Ser Gln Val Cys Glu Lys
            195                 200                 205

GTG ACC AAT TCT GTA TCC TCC AAG CTG CAA CCT TAT TTC CAG ACT CTG   672
Val Thr Asn Ser Val Ser Ser Lys Leu Gln Pro Tyr Phe Gln Thr Leu
            210                 215                 220

CCA GTA ATG ACC AAA ATA GAT TCT GTG GCT GGA ATC AAC TAT GGT CTG   720
Pro Val Met Thr Lys Ile Asp Ser Val Ala Gly Ile Asn Tyr Gly Leu
225             230                 235                 240

GTG GCA CCT CCA GCA ACC ACG GCT GAG ACC CTG GAT GTA CAG ATG AAG   768
Val Ala Pro Pro Ala Thr Thr Ala Glu Thr Leu Asp Val Gln Met Lys
                245                 250                 255

GGG GAG TTT TAC AGT GAG AAC CAC CAC AAT CCA CCT CCC TTT GCT CCA   816
Gly Glu Phe Tyr Ser Glu Asn His His Asn Pro Pro Pro Phe Ala Pro
            260                 265                 270

CCA GTG ATG GAG TTT CCC GCT GCC CAT GAC CGC ATG GTA TAC CTG GGC   864
Pro Val Met Glu Phe Pro Ala Ala His Asp Arg Met Val Tyr Leu Gly
            275                 280                 285

CTC TCA GAC TAC TTC TTC AAC ACA GCC GGG CTT GTA TAC CAA GAG GCT   912
Leu Ser Asp Tyr Phe Phe Asn Thr Ala Gly Leu Val Tyr Gln Glu Ala
            290                 295                 300

GGG GTC TTG AAG ATG ACC CTT AGA GAT GAC ATG ATT CCA AAG GAG TCC   960
Gly Val Leu Lys Met Thr Leu Arg Asp Asp Met Ile Pro Lys Glu Ser
305             310                 315                 320

AAA TTT CGA CTG ACA ACC AAG TTC TTT GGA ACC TTC CTA CCT GAG GTG  1008
Lys Phe Arg Leu Thr Thr Lys Phe Phe Gly Thr Phe Leu Pro Glu Val
            325                 330                 335

GCC AAG AAG TTT CCC AAC ATG AAG ATA CAG ATC CAT GTC TCA GCC TCC  1056
Ala Lys Lys Phe Pro Asn Met Lys Ile Gln Ile His Val Ser Ala Ser
            340                 345                 350
```

FIG. 8B

```
ACC CCG CCA CAC CTG TCT GTG CAG CCC ACC GGC CTT ACC TTC TAC CCT  1104
Thr Pro Pro His Leu Ser Val Gln Pro Thr Gly Leu Thr Phe Tyr Pro
        355                 360                 365

GCC GTG GAT GTC CAG GCC TTT GCC GTC CTC CCC AAC TCC TCC CTG GCT  1152
Ala Val Asp Val Gln Ala Phe Ala Val Leu Pro Asn Ser Ser Leu Ala
        370                 375                 380

TCC CTC TTC CTG ATT GGC ATG CAC ACA ACT GGT TCC ATG GAG GTC AGC  1200
Ser Leu Phe Leu Ile Gly Met His Thr Thr Gly Ser Met Glu Val Ser
385                 390                 395                 400

GCC GAG TCC AAC AGG CTT GTT GGA GAG CTC AGG CTG GAT AGG CTG CTC  1248
Ala Glu Ser Asn Arg Leu Val Gly Glu Leu Arg Leu Asp Arg Leu Leu
                405                 410                 415

CTG CAA CTG AAG CAC TCA AAT ATT GGC CCC TTC CCG GTT GAA TTG CTG  1296
Leu Gln Leu Lys His Ser Asn Ile Gly Pro Phe Pro Val Glu Leu Leu
            420                 425                 430

CAG GAT ATC ATG AAC TAC ATT GTA CCC ATT CTT GTG CTG CCC AGG GTT  1344
Gln Asp Ile Met Asn Tyr Ile Val Pro Ile Leu Val Leu Pro Arg Val
            435                 440                 445

AAC GAG AAA CTA CAG AAA GGC TTC CCT CTC CCG ACG CCG GCC AGA GTC  1392
Asn Glu Lys Leu Gln Lys Gly Phe Pro Leu Pro Thr Pro Ala Arg Val
        450                 455                 460

CAG CTC TAC AAC GTA GTG CTT CAG CCT CAC CAG AAC TTC CTG CTG TTC  1440
Gln Leu Tyr Asn Val Val Leu Gln Pro His Gln Asn Phe Leu Leu Phe
465                 470                 475                 480

GGT GCA GAC GTT GTC TAT AAA TGAAGGCACC AGGGGTGCCG GGGGCTGTCA     1491
Gly Ala Asp Val Val Tyr Lys
                485

GCCGCACCTG TTCCTGATGG GCTGTGGGGC ACCGGCTGCC TTTCCCCAGG GAATCCTCTC

CAGATCTTAA CCAAGAGCCC CTTGCAAACT TCTTCGACTC AGATTCAGAA ATGATCTAAA

CACGAGGAAA CATTATTCAT TGGAAAAGTG CATGGTGTGT AT                  1653
```

SYNTHETIC PEPTIDES WITH BACTERICIDAL ACTIVITY AND ENDOTOXIN NEUTRALIZING ACTIVITY FOR GRAM NEGATIVE BACTERIA AND METHODS FOR THEIR USE

This invention was made with support from The Cystic Fibrosis Foundation and with government support under 2R01-A1-26159 awarded by the National Institute of Health. The Government has certain rights in the invention.

BACKGROUND OF THE INVENTION

The microbicidal mechanisms of polymorphonuclear leukocytes (PMNL) depend on the products of phagocytosis-stimulated oxidative metabolism for killing of many bacteria. Oxygen-dependent intracellular killing of *staphylococcus aureus, Serratia marcescens, Proteus mirabilis, Escherichia coli,* and *Pseudomonas cepacia* is indicated because these bacteria are not killed by PMNL in which the oxidative burst is rendered nonfunctional. PMNL from patients with Chronic Granulomatous Disease (CGD), an inherited deficiency of the oxidative response, are unable to kill the above bacteria and CGD patients have a corresponding susceptibility to infection by these same bacteria. Gallin, *Ann. Int. Med.*, 99:657 (1983); Johnston et al., *Ped. Clin. of N. Amer.*, 24:365 (1977); Holmes et al., *Lancet*, 1:1225 (1966); Quie et al., *J. Clin. Invest.*, 46:668 (1967); Bottone et al., *J. Clin. Med.*, 1:425 (1975); and Holmes et al., *J. Clin. Invest.*, 46:1422 (1967). The bacteria listed above are also not killed by normal human PMNL incubated in an anaerobic environment. Mandell, *Infect. Immun.*, 9:337 (1974).

Conversely, a significant contribution of oxygen-independent microbicidal mechanisms is invoked when the rate and extent of intracellular killing by anaerobic normal human PMNL, PMNL from CGD patients, or aerobically-incubated normal human PMNL are equal. *Salmonella typhimurium* are killed by CGD cells at a normal rate and at a near normal rate by control PMNL incubated anaerobically. Weiss et al., *J. Clin. Invest.*, 69:959 (1982); Mandell, cited supra.; and Okamura et al., *Infect. Immun.*, 36:1086 (1982). Neisseria gonorrhoea are killed by CGD cells as well as they are by normal PMNL and are killed at a normal rate by anaerobic normal PMNL. Rest et al., *Infect. Immun.*, 36:737 (1982); and Casey et al., *Infect. Immun.*, 52:384, (1986). It has been established that PMNL from patients with CGD retain a normal ability to kill *Pseudomonas aeruginosa* strains and, when incubated under anaerobic conditions, normal human PMNL kill *P. aeruginosa* as well as they do in an aerobic environment. Holmes, *Reticulo. Soc.*, 22:87 (1978); and Mandell, cited supra. The evidence strongly suggests that intracellular killing of these bacteria by oxygen-independent mechanisms depends on the toxicity of the contents of cytoplasmic granules from PMNL. Weiss et al., *J. Clin. Invest.*, 69:959 (1982); Holmes, *Reticulo. Soc.*, 22:87 (1978); and Rest, *Infect. Immun.*, 25:574 (1979). Bactericidal factors which are implicated in oxygen-independent mechanisms have been purified from the extracts of these cytoplasmic granules.

Weiss et al. have described a 58–60 kD bactericidal/permeability increasing protein (B/PI) active against *S. typhimurium* and *E. coli*. Weiss et al., *J. Biol. Chem.*, 253:2664 (1978). Shafer et al. have described the purification of a 56 kD cationic antibacterial protein (CAP57) and a 37 kD protein (CAP37) with activity towards *S. typhimurium*. Shafer et al., *Infect. Immun.*, 45:29 (1984). A 55 kD glycoprotein (BP55) having potent bactericidal activity towards *P. aeruginosa* has been purified. Hovde et al., *Infect. Immun.*, 54:142 (1986). Intracellular killing of *N. gonorrhoea* has been traced to the nonenzymatic bactericidal activity of cathepsin G. Bangalore et al., *J. Biol. Chem.*, 265:13584 (1990). The cationic peptide defensins are also strong candidates for the oxygen-independent microbicidal mechanisms of PMNL. Lehrer et al, *Ann. Rev. of Immunol.*, 11:105 (1993). Two apparently novel microbicidal substances, azurocidin and p29b, have also been shown to have bactericidal activity. Gabay et al., *Proc. Natl. Acad. Sci.*, 86:5610 (1989); and Campanelli et al., *J. Clin. Invest.*, 85:904 (1990). Although azurocidin and cathepsin G kill *P. aeruginosa*, they are 80 to 140-fold less active than BP55. The evidence that azurocidin and CAP37 are the same protein has recently been reviewed. Wasiluk et al., *Infect. Immun.*, 59:3193 (1991).

It is likely that BP55, B/PI and CAP57 are the same molecule based on comparison of N-terminal amino acid sequences. The identical amino-terminal amino acid sequences of BP55, B/PI and CAP57 correspond to the amino acid sequence deduced from the nucleotide sequence of a full length cDNA clone for B/PI. In addition, a monoclonal antibody to CAP57 was shown to crossreact with B/PI. Spitznagel, *J. Clin, Invest.*, 86:1381 (1990). B/PI are primarily bactericidal toward gram-negative bacteria. Studies of CAP57 and B/PI have concentrated on studies of *E. coli* and *S. typhimurium*. The studies of BP55 evolved from the demonstration that *P. aeruginosa* was killed by an oxygen-independent mechanism. Although there was no evidence of permeability increase in *P. aeruginosa*, the inner membrane functions of *P. aeruginosa*, such as amino acid transport, ceased immediately upon exposure to BP55. Hovde et al., *Infect. Immun.*, 52:90 (1986). Studies of *E. coli* have recently confirmed the loss of amino acid transport function in the lethal effects of B/PI at pH 6.0. Mannion et al., *J. Clin. Invest.*, 85:853 (1990). A reference to B/PI will be understood to also refer to BP55.

An important persistent difference of the studies of *P. aeruginosa* with BP55 is that, whether smooth or rough, serum-resistant or serum-sensitive, all strains of Pseudomonas thus far studied are equally sensitive to killing by BP55. Siefferman et al., *Infect. and Immun.*, 59:2152 (1991). By contrast, studies of *S. typhimurium* and *E. coli* have consistently shown that resistance to CAP57 and B/PI increases dramatically with the length of the O polysaccharide chains on the LPS of the respective bacterial outer membranes. Gabay et al., cited supra.; Campanelli et al., cited supra; Wasiluk et al., cited supra.; Spitznagel, cited supra.; Elsbach et al., *Curr. Opinion in Imm.*, 5:103 (1993); Ooi et al., *J. Biol. Chem.*, 262:14891 (1987); Gray et al., *J. Biol. Chem.*, 264:9505 (1989); Hovde et al., *Infect. Immun.*, 52:90 (1986); Mannion et al., cited supra.; Siefferman et al., cited supra.; Farley et al., *Infect. Immun.*, 56:1589 (1988); and Weiss et al., *Infect. Immun.*, 51:594 (1986).

Recent studies of B/PI (BP55) have adjusted its molecular mass to 55 kD and turned to its ability to neutralize the endotoxin effects of *E. coli* LPS. The ability to neutralize endotoxin, as well as the bactericidal function, has been localized to the amino-terminal half of the B/PI molecule of 199 amino acids. The native B/PI molecule ($nBPI_{55}$) has been shown to neutralize the pyrogenicity of LPS for rabbits, the ability of LPS to initiate the coagulation pathway of the Limulus amoebocyte lysate, and the ability of LPS to cause tumor necrosis factor (TNF) release from human monocytes. Marra et al., *J. Immunol.*, 148:532 (1992); and Marra et al., *J. Immunol.*, 144:662 (1990). The carboxyl-terminal half of nBPI$_{55}$ inhibits the ability of LPS to cause TNF release from whole blood and is active in the inhibition of effects of LPS on the Limulus amoebocyte lysate. Ooi et al., *J. Exp. Med.,* 174:649 (1991).

Neutralization of the ability of LPS to activate in the Limulus assay has also been demonstrated for a 25 kD amino-terminal proteolytic fragment of native B/PI (nBPI$_{25}$) and for a 23 kD recombinant form (rBPI$_{23}$) of the same region of B/PI. Ooi et al., *J. Exp. Med.,* 174:649 (1991); and Weiss et al., *J. Clin. Invest.,* 90:1122 (1992). The nBPI$_{25}$ fragment and the rBPI$_{23}$ product consist of the first 199 amino acids of the amino terminus of B/PI. Both are capable of killing *E. coli* and of binding to LPS or lipid A while neutralizing the ability of endotoxin to upregulate the expression of complement receptors on neutrophils and to cause TNF release from whole blood. Elsbach et al., cited supra.; and Weiss et al., *J. Clin. Invest.,* 90:1122 (1992). High affinity binding of LPS by rBPI$_{23}$ has been demonstrated. Gazzano-Santoro et al., *Infect. Immun.,* 60:4754 (1992); and Heumann et al., *J. Infect. Dis.,* 167:1351 (1993).

The accumulated evidence suggests that the binding site for BP55, CAP57, and B/PI is the lipid A moiety of the outer membrane lipopolysaccharide (LPS) of gram-negative bacteria. LPS is anchored in the outer membrane by noncovalent cross-bridging of adjacent LPS molecules with divalent cations (MG$^{++}$ and Ca$^{++}$) which are tightly bound to anionic phosphate groups clustered at the base of the polysaccharide chain near the hydrophobic lipid A moiety. Hancock, *Ann. Rev. Microbiol.,* 38:237 (1984). B/PI and CAP57 appear to compete with Mg$^{++}$ and Ca$^{++}$ for these surface sites and binding is largely determined by the accessibility of these anionic groups. Binding of B/PI can be inhibited by the presence of 2.5 mM Mg$^{++}$ and bound B/PI can be removed by the addition of 80 mM Mg$^{++}$. Weiss et al., *J. Biol. Chem.,* 253:2664 (1978); and Weiss et al., *J. Clin. Invest.,* 71:540 (1983). The presence of free LPS will inhibit binding of BP55, B/PI and CAP57. Wasiluk et al., cited supra.; Weiss et al., *J. Biol. Chem.,* 253:2664 (1978); and Shafer et al., *Infect. Immun.,* 43:834 (1984).

Studies of two strains of *S. typhimurium* which differed only in the degree of substitution of the 4'-phosphate of lipid A with 4-amino-L-arabinose provide the only direct evidence of the interaction of antibacterial protein with ionic groups of the lipid A and inner core region of LPS. A strain with 70% substitution of the 4' phosphate was significantly more resistant to killing by CAP57 than was the isogeneic strain. Shafer et al., *Infect. Immun.,* 43:834 (1984). Others have shown that the terminal phosphate group of lipid A is important for binding of nBPI$_{55}$. In vivo studies in mice of nBPI$_{55}$ and rBPI$_{23}$ have shown that both are effective in the treatment of gram-negative pneumonia. Kelly et al., *Surgery,* 114:140 (1993).

Thus, there is a need for compositions effective to treat and prevent gram-negative infections and endotoxin shock associated with gram-negative infection. There is a need to develop large amounts of therapeutically active peptides that can be used to treat gram-negative infections and endotoxin shock.

SUMMARY OF THE INVENTION

The invention provides biologically active peptides having an amino acid sequence derived from or corresponding to regions of B/PI. The biologically active peptides are preferably 10 to 100 amino acids long and have bactericidal activity and/or endotoxin neutralizing activity. The bactericidal peptides preferably kill strains of Pseudomonas but can also kill *S. aureus*. The peptides can be modified by the addition of cysteine residues and form dimers or cyclic peptides. Peptides can also be attached to carrier molecules such as serum albumin to form peptide conjugates useful to generate monoclonal antibodies and in pharmaceutical compositions.

The peptides are useful in methods of treating bacterial infection and endotoxin shock. The methods of the invention involve administering a pharmaceutical composition to an animal to inhibit the bacterial infection or decrease the symptoms of endotoxin shock. The pharmaceutical composition includes an amount of a bactericidal and/or endotoxin neutralizing peptide sufficient to inhibit infection or decrease the symptoms of endotoxin shock. The peptides are in admixture with a pharmaceutically acceptable carrier.

The peptides are also useful as a coating on a prosthetic or implantable device to inhibit bacterial infection associated with introduction of such devices into the body. The peptide is attached to the surface of the prosthetic device in an amount effective to inhibit growth of the bacteria, especially *Pseudomonas spp*. The peptide can optionally be coupled to a carrier molecule before attachment to the surface of the prosthetic device.

The biologically active peptides of the invention can be prepared by automated synthesis or recombinant DNA technology. Thus, the invention also provides for DNA sequences coding for the biologically active peptides of the invention.

BRIEF DESCRIPTION OF THE FIGURES

FIG. 4A represents a nucleotide sequence coding (SEQ ID NO:1) for B/PI and the predicted amino acid sequence (SEQ ID NO:2).

FIG. 8, 8A, 8B is the entire sequence of a cDNA (SEQ ID NO:3)encoding a 55,000 dalton B/PI protein (SEQ ID NO:4).

DETAILED DESCRIPTION OF THE INVENTION

Figure 1:
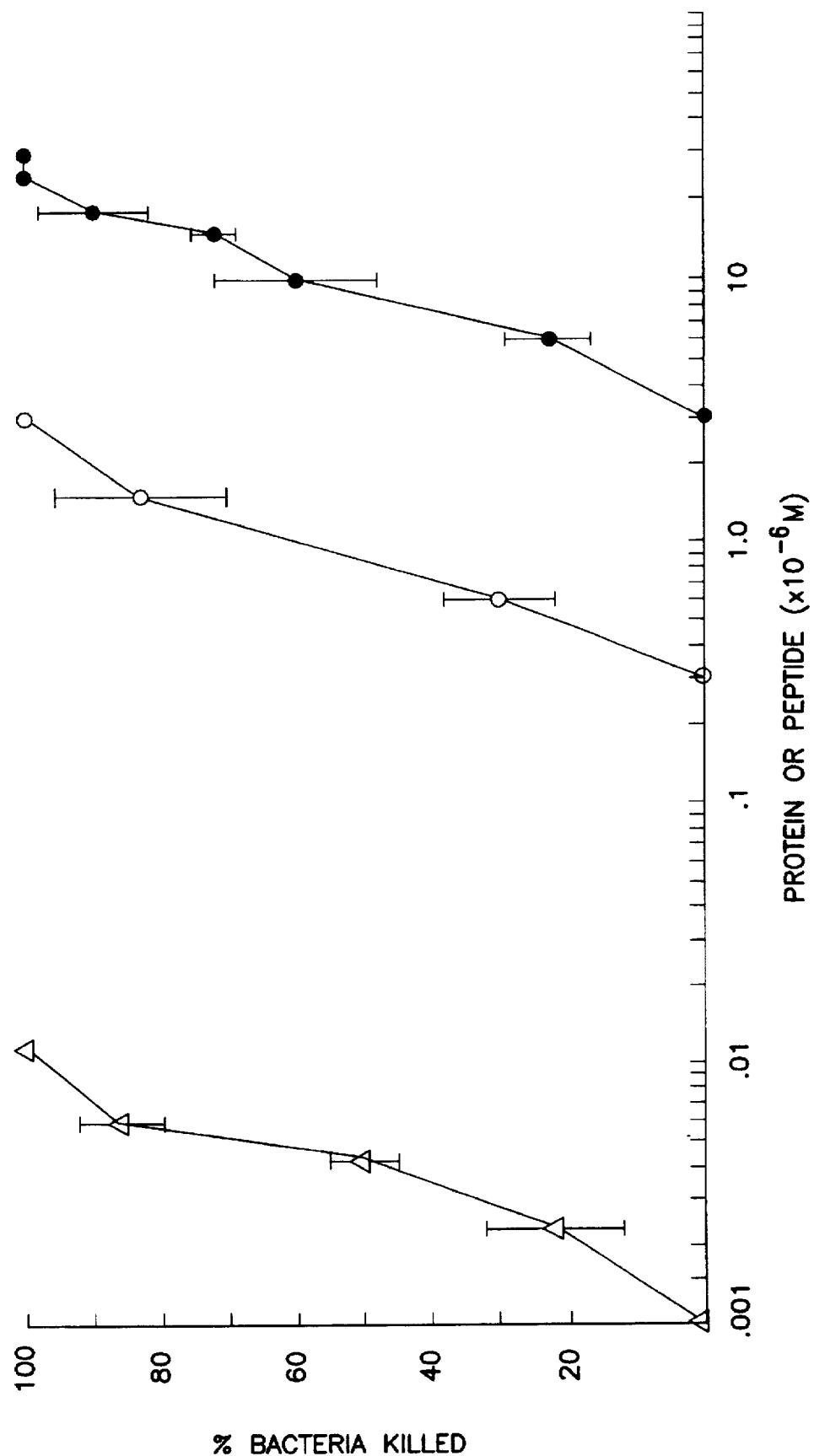
FIG. 1 shows the dose response for the bactericidal effects of peptides C#90–99 (o—o) and #90–99 (●—●) and B/PI (Δ—Δ) toward 5×10$^6$ CFU of *P. aeruginosa* type 1 incubated at pH 5.6. Values for C#90–99 are the mean of three experiments ± one standard error of the mean.

The invention provides for peptides derived from a neutrophil bacterial permeability protein (B/PI). The peptides are those that are biologically active for bacterial killing or endotoxin neutralization or both. Preferably, the peptides are about 10 to about 100 amino acids long and contain hydrophilic regions based upon the hydropathy plot of B/PI of Table 1. The peptides can be modified in many ways including by addition of N- and/or C-terminal cysteine residues. The peptides are useful in pharmaceutical compositions to treat and prevent bacterial infections and endotoxin shock. The peptides may also be useful to prevent the growth of bacteria on surfaces. The invention, therefore, also provides for methods of using the peptides to treat and prevent bacterial infection and endotoxin shock.

A. Isolation of Bacteria Permeability Protein from Neutrophils and Selection of Biologically Active PePtides A bactericidal protein (B/PI) having a molecular weight of 55,000 daltons as determined by SDS-PAGE can be isolated from human neutrophils. Briefly, a granular extract from human neutrophils can be separated by Orange A (Amicon Corp., Beverly, Mass.) column chromatography. Fractions having bactericidal activity for *P. aeruginosa* can be pooled and separated by cation exchange chromatography. Fractions having bactericidal activity can be pooled and further separated by molecular-sieving chromatography. Fractions having bactericidal activity can be pooled and characterized by SDS-PAGE. The B/PI protein can be further characterized by its amino acid sequence. A cDNA sequence coding for B/PI generated by standard methods provides the predicted amino acid sequence for B/PI as shown in FIG. 4 and FIG. 8. Isolated native B/PI has the N-terminal amino acid sequence of:

VNPGVVVRISQKGLDYASQQG (SEQ ID NO:5)

which is in agreement with the predicted amino acid sequence for the N-terminal region of B/PI shown in FIG. 4 and FIG. 8.

Once the predicted amino acid sequence of B/PI is known, biologically active peptides having an amino acid sequence derived from or corresponding to that of B/PI can be selected and/or modified. A peptide sequence that is derived from or corresponding to a peptide from B/PI has about 90–100% sequence identity and has at least one functional activity in common with B/PI. The peptide sequence can be selected based on several criteria including the biological activity, hydrophilicity, and size. Biologically active peptides include those that are bactericidal, those that have endotoxin neutralizing activity, and those that have both activities.

Bactericidal activity can be evaluated against a variety of bacteria such as *Pseudomonas spp* including *aeruginosa* and *P. cepacia*, *E. coli B*, and *Staphylococcus aureus*. The preferred organism is *P. aeruginosa*. Bactericidal activity is determined by identifying the effective dose for killing as the molar concentration of the peptide which results in at least a 60% killing of the bacteria, as determined by standard methods. Preferably, the peptide has an effective dose at a concentration of about $1\times10^{-4}$M to about $1\times10^{-10}$M, and more preferably $1\times10^{-7}$M to $1\times10$–9M . Peptides corresponding to and/or derived from B/PI that were considered not bactericidal did not kill P. aeruginosa at concentrations of $10^{-4}$M or less at a pH of 5.6. The effective dose for bactericidal activity of B/PI is seen at about $10^{-9}$ to $10^{-1}$M . Bactericidal activity can also be determined by calculating a lethal dose 50 ($LD_{50}$) using standard methods. The $LD_{50}$ is that amount of peptide or protein that kills 50% of the bacteria when measured using standard dose response methods. See FIG. 1. A bactericidal peptide preferably has an $LD_{50}$ of about $10^{-4}$M to about $10^{-9}$M , more preferably about $10^{-7}$ to $10^{-9}$M .

The peptide selected can also have endotoxin neutralizing activity. Endotoxin neutralizing activity can be measured by determining the molar concentration at which the peptide completely inhibits the action of lipopolysaccharide in an assay such as the Limulus amoebocyte lysate assay (LAL) (Sigma Chemicals, St. Louis, Mo.) or the chromogenic LAL 1000 test (Biowhittacker, Walkersville, Md.). Endotoxin neutralizing activity can also be measured by calculating an inhibitory dose 50 ($LD_{50}$) using standard does response methods. An inhibitory dose 50 is that amount of peptide that can inhibit 50% of the activity of endotoxin. Endotoxin activity can also be measured by determining the amount of release of tumor necrosis factor alpha (TNFα) from a macrophage cell line or by evaluating the symptoms of shock in animals. Peptides preferably neutralized endotoxin at a molar concentration of about $1\times10^{-4}$M to about $10^{-8}$M , more preferably about $10^{-5}$M to about $10^{-6}$M . The native B/PI molecule has endotoxin neutralizing activity at about $10^{-8}$M. Peptides derived and/or modified from B/PI that were considered to not have endotoxin neutralizing activity did not neutralize endotoxin at a molar concentration of $10^{-4}$ or less.

Figure 6:
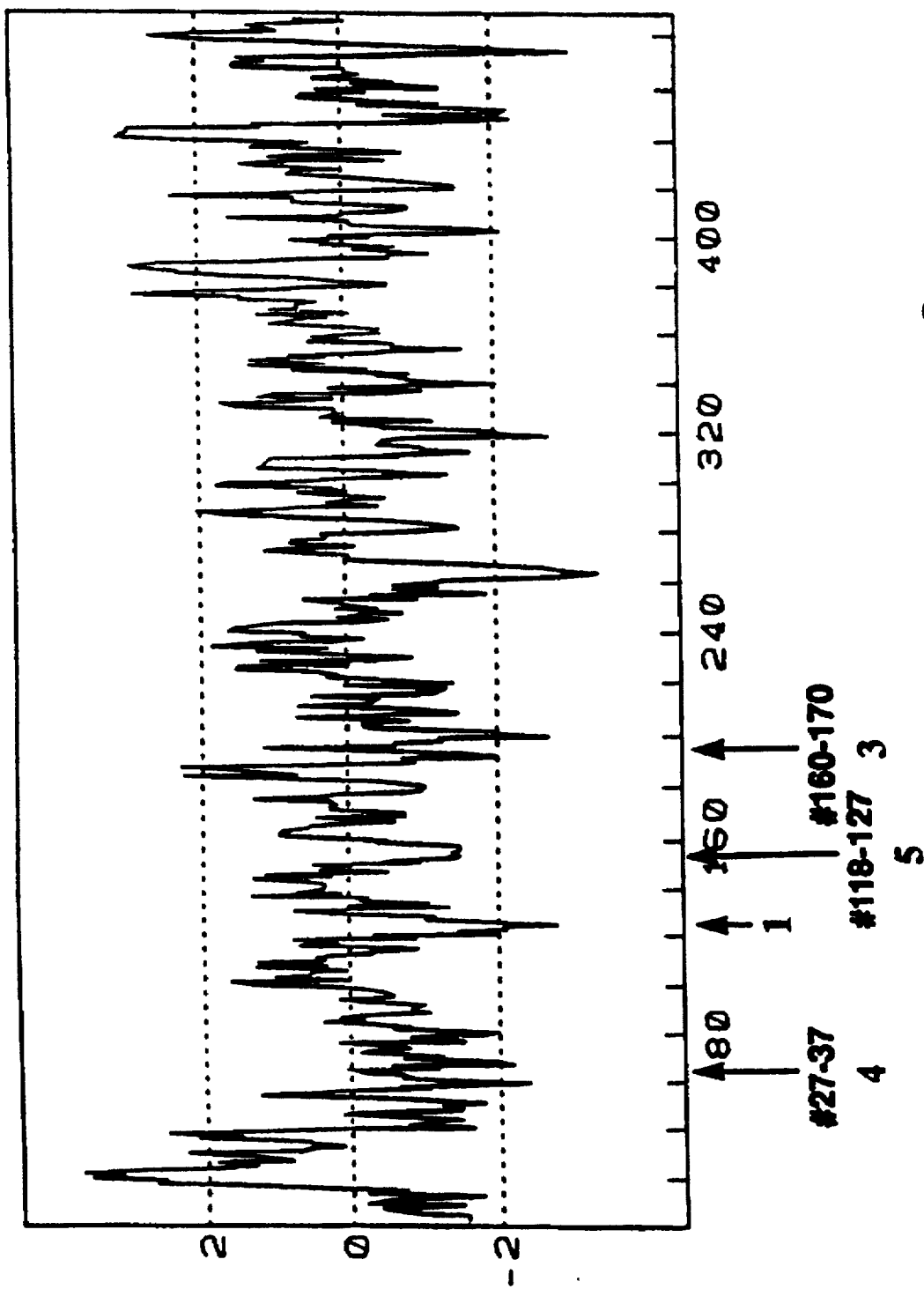
FIG. 6 is a hydropathy plot of B/PI based upon the average of 5 amino acid stretches.

Peptides selected can also have a hydrophilic character as determined by a hydropathy plot, according to the method of Kyte and Doolittle, *J. Mol. Biol.*, 157:105 (1982) see FIG. 6. Hydropathy plots can be used to calculate a hydropathy index for peptides and identify regions of polypeptides that are hydrophilic in character. Hydrophilic peptides of B/PI and the hydropathy index for those peptides are shown in Table 1.

TABLE I

HYDROPATHY INDICES OF PEPTIDES DERIVED FROM OR CORRESPONDING TO B/PI

|  | Derived from B/PI | Net Hydropathy Index$_b$ |
|---|---|---|
| #90-99 | kwkaqkrflk (SEQ ID NO:6) | −16.1 |
| C#90-99 | ckwkaqkrflk (SEQ ID NO:7) | −13.6 |
| #90-102 | kwkaqkrflkmsq (SEQ ID NO:8) | −15.4 |
| #86-99 | kisgkwkaqkrflk (SEQ ID NO:9) | −16.7 |
| C86-99 | ckisgkwkaqkrflk (SEQ ID NO:10) | −14.2 |
| Hybrid | efysenhhnpkwkaqkrflk (SEQ ID NO:11) | −31.7 |
| CHydrid | cefysenhhnpkwkaqkrflk (SEQ ID NO:12) | −34.2 |
| Signal | mrenmargpc (SEQ ID NO:13) | −9.9 |
| #27-37 | kelkrikipdy (SEQ ID NO:14) | −13.3 |
| #118-127 | klgsnptsgk (SEQ ID NO:15) | −12.2 |
| #160-170 | kkiesalmkm (SEQ ID NO:16) | −12.0 |
| C#227-236 | cefysenhhnp(g) (SEQ ID NO:17) | −19.2 |
| C#418-427 | cneklqkgfpl (SEQ ID NO:18) | −7.4 |

$_b$The summation of Kyte and Doolittle hydropathy indices for each amino acid of the sequence Hydrophilic peptides are those that have a net hydropathy index of at least about −1. Some of the hydrophilic peptides identified can also be biologically active for either bactericidal activity, endotoxin neutralizing activity, or both.

The peptides of the invention preferably have a size of about 10 amino acids to about 100 amino acids, more preferably about 10 to 40 amino acids. A peptide having about 10 amino acids is the minimum size peptide shown to have endotoxin neutralizing activity and/or bactericidal activity. Peptides with 20 to 40 amino acids include those peptides that have both endotoxin neutralizing and bactericidal activities.

Some of the peptides derived from B/PI only exhibit bactericidal activity. Other peptides have both bactericidal and endotoxin neutralizing activity. Peptides having a sequence corresponding to or derived from B/PI and that have bactericidal activity preferably include at least the amino acid sequence KWKAQKRFLK (SEQ ID NO:6) Suitable examples of peptides having bactericidal activity include:

KWKAQKRFLK (#90-99) (SEQ ID NO:6;
KISGKWKAQKRFLKMSGNF (SEQ ID NO:19) (86-104);
NANIKISGKWKAQKRFLKMSGNFDLSI (82-108) (SEQ ID NO:20); and
EFYSENHHNPKWKAQKRFLK (Hybrid) (SEQ ID NO:11)

The preferred bactericidal peptides are those that have bactericidal activity for *P. aeruginosa* at an effective dose of about $10^{-7}$M to about $10^{-9}$M , have about 10 to about 40 amino acids and include the amino acid sequence of KWKAQKRFLK. The especially preferred peptides are those including the amino acid sequence of residues 82–108 of B/PI.

Some of the peptides derived from B/PI only have endotoxin neutralizing activity. Other peptides have both bactericidal and endotoxin neutralizing activity. Suitable examples of peptides derived from or corresponding to sequences of B/PI and that have endotoxin neutralizing activity are:

VNPGVVVRISQKGLDYASQQGTAALQ (1-26) (SEQ ID NO:21);
KKIESALRNKM (160-170) (SEQ ID NO:16);
EFYSENHHNP(G) (227-236) (SEQ ID NO:22);
NEKLQKGFPL (418-427) (SEQ ID NO:23); and
NANIKISGKWKAQKRFLKMSGNFDLSI (SEQ ID NO:20) (82-108).

The preferred endotoxin neutralizing peptides neutralize endotoxin at a concentration of about $10^{-5}$M to $10^{-8}$M and have about 10 to 40 amino acids. The especially preferred peptides are peptides including amino acids 1–26 or 82–108 of B/PI.

Some peptides have both endotoxin neutralizing activity and bactericidal activity. Suitable examples of peptides derived from or corresponding to B/PI that have both biological activities include:

CEFYSENHHNPKWKAQKRFLK (Hybrid) (SEQ ID NO:12);
KWKFKQRALK (random 90-99) (SEQ ID NO:24);
NANIKISGKWKAQKRFLKMSGNFDLSI (82-108) (SEQ ID NO:20); and
KISGKWKAQKRFLKMSGNF (#86-104) (SEQ ID NO:19).

The preferred peptide having both bactericidal and endotoxin neutralizing activity has about 10 to 40 amino acids and includes at least the amino acid sequence of residues 90–99 of B/PI. The especially preferred peptide having both biological activities is the peptide including amino acid residues 82–108. The preferred peptides are also soluble in water or DMSO and are not toxic to eukaryotic cells.

B. Modifications of the Biologically Active Peptides

The biologically active peptides derived from or corresponding to regions of B/PI can also be modified in a variety of ways to form biologically active derivatives or analogs of the peptides. These modifications include addition, substitution or deletion of amino acids. Addition of amino acids includes, for example, the formation of dimers, cyclic, or hybrid peptides as well as attachment of the peptides to carrier molecules. Substitution of amino acid residues include conservative amino acid substitutions.

Peptides derived from or corresponding to regions of B/PI can be modified by the addition of amino acids. For example, cysteine residues can be added preferably at the N- and/or C-terminal ends of the peptide. However, some peptides can have at least two cysteine residues, at least one of which is not located at the N- and/or C-terminal amino acid so that upon formation of an intra chain disulfide bond, a cyclic portion of the peptide is formed. The cysteine residues can be used to form a dimer or cyclic form of the peptide. Addition of cysteine residues at the N- and/or C-terminal end of the peptide can also result in enhanced bactericidal activity of peptides including amino acid sequence KWKAQKRFLK (SEQ ID NO:6). While not meant to limit the invention in any way, it is believed the enhancement of biological activity is not dependent on disulfide bond formation as elimination of a free reduced sulfhydryl group did not decrease biological activity.

Suitable examples of peptides that have biological activity and have N- and/or C-terminal cysteine residues and can form either dimers or cyclic compounds include:

CKWKAQKRFLK (C#90-99) (SEQ ID NO:7);
CKISGKWKAQKRFLK (C#86-99(SEQ ID NO:10) or (dimer of C#86-99);
CKWKAQKRFLKC (C#90-99C) (SEQ ID NO:10);
Cyclic CKWKAQKRFLKC (cyclic C#90-99C) (SEQ ID NO:25);
KWKAQKRFLKC (#90-99C) (SEQ ID NO:26);
CKWKAQKRFLKMSG (C#90-102) (SEQ ID NO:27);
CEFYSENHHNPKWKAQKRFLK (Chybrid) (SEQ ID NO:12);
CEFYSENHHNP(G) (C#227-236) (SEQ ID NO:17);
CNEKLQKGFPL (C#418-427) (SEQ ID NO:18);
CNANIKISGKWKAQKRFLKMSGNFDLSIC (C#82-108C) (SEQ ID NO:28); and
CKISGKWKAQKRFLKMSGNFC (C#86-104C) (SEQ ID NO:29).

The especially preferred peptide modified with an N- and/or C-terminal cysteine is one that includes the amino acid sequence KWKAQKRFLK (SEQ ID NO:6), such as C#90-99C, C#82-108C or C#86-104C in linear or cyclic form.

Peptides including cysteine residues can form either dimers or cyclic compounds under conditions that favor formation of intrachain or interchain disulfide bonds. If the peptide contains at least one cysteine group either internally or at the N- and/or C-terminal amino acid, dimers can be formed under conditions that favor interchain disulfide bond formation. Interchain disulfide bonds are favored when peptide contains a single cysteine residue and is present in at a high enough concentration that dimers can readily be formed, preferably about 3 mM. Peptides having N- and C-terminal cysteines or one N- or C-terminal cysteine and one internal cysteine can form cyclic compounds under conditions that favor the formation of intrachain disulfide bonds. Intrachain disulfide bonds are favored when the peptide has at least 2 cysteine residues and is present at a dilute concentration preferably such as 0.1 mg/ml (1 µM or less) or less.

When the peptide has one N- or C-terminal cysteine and an internal cysteine residue, a peptide with cyclic portion can be formed, the cyclic portion preferably has about 10 amino acids to 40 amino acids and includes the amino acid sequence:

KWKAQKRFLK (SEQ ID NO:6).

When the cysteine residues are at the N- and C-terminals of the peptide, a cyclic peptide if formed, preferably having about 10 to 40 amino acids and the amino acid sequence:

KWKAQKRFLK (SEQ ID NO:6).

The especially preferred cyclic peptides have both bactericidal and endotoxin neutralizing activity and the sequence:

CKISGKWKAQKRFLKMSGNFC (C86-104C) (SEQ ID NO:29).

CKWKAQKRFLKC (C90-99C) (SEQ ID NO:25), or

CNANIKISGKWKAQKRFLKMSGNFDLSIC (C82-108C) (SEQ ID NO:28).

Addition of amino acid residues can also include coupling of the biologically active peptides to a larger molecular weight carrier protein to form a peptide conjugate. Coupling of the peptide can take place with addition of an amino acid, preferably cysteine or glycine, at the N- and/or C-terminus of the peptide to serve as a point of attachment to the carrier. Attachment of peptides to carrier molecules is conducted by standard methods known to those of skill in the art. Alternatively, the peptide can be attached directly to the carrier. The carrier molecule is a large molecular weight molecule, such as keyhole limpet hemocyanin (KLH) or bovine serum albumin (BSA). Attachment of the peptide can occur at multiple locations on the carrier molecule. These peptide conjugates can have biological activity similar to that of the corresponding unconjugated peptide and/or can be useful in pharmaceutical compositions or for formation of monoclonal antibodies to biologically active peptides derived from or corresponding to B/PI.

Additionally, amino acids or peptides can be combined with one another to form hybrid peptides. Hybrid peptides include those that have amino acid sequences from two different regions of the B/PI molecule as well as fusion proteins such as a peptide fused to another protein such as B-galactosidase. For example, a peptide having bactericidal activity can be combined with a peptide having endotoxin neutralizing activity to form a hybrid peptide. A hybrid peptide so formed has at least one biological activity and preferably has both bactericidal and endotoxin neutralizing activity. The hybrid peptide can be formed by the formation of disulfide bonds between peptides having two different amino acid sequences or by the formation of a peptide bond between the N-terminal amino acid of one peptide and the C-terminal amino acid of the other peptide. A hybrid peptide can also include a cyclic portion as described previously.

The hybrid peptide preferably includes an endotoxin neutralizing peptide having an amino acid sequence selected from the group consisting of:

CEFYSENHHNP (C#227-236) (SEQ ID NO:30);

VNPGVVVRISQKGLDYASQQGTAALQ (1-26) (SEQ ID NO:21);

CVNPGVVVRISQKGLDYASQQGTAALQ (C1-26) (SEQ ID NO:31); and

SDSFKIKHLGKGHYSFYSMDIREFQ (#38-62) (SEQ ID NO:32).

The hybrid peptide preferably also includes a bactericidal peptide having a sequence selected from the group consisting of:

KWKAQKRFLK (90-99) (SEQ ID NO:6);

CKWKAQKRFLKC (C90-99C) (SEQ ID NO:25);

NANIKISGKWKAQKRFLKMSGNFDLSI (82-108) (SEQ ID NO:20);

CNANIKISGKWKAQKRFLKMSGNFDLSIC (C82-108C) (SEQ ID NO:28);

CKISGKWKAQKRFLKMSGNFC (C86-104C) (SEQ ID NO:29); and

KISGKWKAQKRFLKMSGNF (86-104) (SEQ ID NO:19).

Hybrid peptides can be further modified by addition of amino acids such as cysteine at the N- and/or C-terminal ends or the formation of cyclic peptides or dimers.

Modifications can also include amino acid substitutions in the sequence of the biologically active peptide. Amino acid substitution can be made as long as the substitutions do not eliminate the biological activity of the peptide. Conservative amino acid substitutions typically can be made without affecting biological activity. Conservative amino acid substitutions include substitution of an amino acid for another amino acid of the same type. Types of amino acids include: (1) basic amino acids such as lysine, arginine, and histidine; (2) hydrophobic amino acids such as leucine, isoleucine, valine, phenylalanine, and tryptophan; (3) non-polar amino acids including alanine, valine, leucine, isoleucine, proline, and methionine; (4) polar amino acids such as serine, threonine, cysteine, tyrosine, asparagine, and glutamine; and (5) positively charged amino acids such as aspartic and glutamic acid. For example, the 93rd amino acid in a peptide having a sequence corresponding to amino acids 90–99 of B/PI can either be alanine, phenylalanine or tryptophan without effecting the bactericidal activity of the peptide.

The effect of other amino acid substitutions or deletions on biological activity can be determined by predicting the effect of the alteration in amino acid sequence on the confirmation or tertiary structure of the peptide using currently available molecular modeling methods or by X-ray crystallography. A peptide having bactericidal or bactericidal and endotoxin neutralizing activity preferably includes at least an amino acid sequence equivalent KWKAQKRFLK (SEQ ID NO:6). An equivalent amino acid sequence to residues 90–99 of B/PI means it is the same sequence or a sequence with a modifications such that the tertiary structure and/or functional activity of the peptide is maintained. For example, a peptide having amino acids corresponding to those of residues 90–99 of B/PI can obtained with the sequence of those residues in random order. For example, bactericidally active peptides having the following sequence:

WKKFKQRALK (SEQ ID NO:35)

KKKWFRLAKQ (SEQ ID NO:36) and

KWKFKKRALK (SEQ ID NO:37)

retain biological activity. In another example, a linear peptide including amino acid residues 90–99 of B/PI modified by N- and C-terminal cysteine residues was converted from a bactericidal peptide to one that has both bactericidal and endotoxin neutralization upon formation of a cyclic peptide.

While not meant to limit the invention in any way, it is believed that amino acid modifications (i.e., additions, substitutions or deletions) can be made to a peptide having bactericidal activity as long as those changes do not change formation of an amphipathic sequence including the amino acids KWKAQKRFLK (SEQ ID NO:6). An amphipathic sequence is one that has positively charged amino acids (+) alternating with one or more (i.e., about 2–3 amino acids) hydrophobic or non-charged amino acids(−). The sequence typically does not have any negatively charged amino acids and preferably includes about 3–6 positively charged amino acids, more preferably 4–5 positively charged amino acids. Optionally, the amphipathic sequence includes at least two positively charged amino acids adjacent to one another to form a bend in the amphipathic sequence when in the conformation of a loop. Examples of peptides with amphipathic sequences including amino acids KWKAQKRFLK (SEQ ID NO:6) of B/PI and that have bactericidal activity include:

KWKAQKRFLK (#90-99) (SEQ ID NO:6) +0+00++00+

WKKFKQRALK (rand. #90-99) (SEQ ID NO:35) 0++0+0+00+

KKKWFRLAKQ (rand. #90-99) (SEQ ID NO:36)
+++00+00+0

KWKFKQRALK (rand. #90-99) (SEQ ID NO:24) +0+0+0+00+

KKKFFRLAKQ (rand. #90-99) (SEQ ID NO:38) +++00+00+0

KKKAFRLAKQ (rand. #90-99) (SEQ ID NO:39) +++00+00+0

Bactericidal peptides having these sequences can be combined with other amino acids to form cyclic compounds or hybrid compounds having both bactericidal and endotoxin neutralizing activities.

Biologically active peptides or derivatives or analogs derived from or corresponding to B/PI can be prepared by automated peptide synthesis or by recombinant DNA technology.

C. Preparation of Biologically Active Peptide Derived from or Corresponding to B/PI Given the amino acid sequence information disclosed herein for B/PI and the state of art in solid phase protein synthesis, essentially pure biologically active peptides can be obtained via chemical synthesis. The principles of solid phase chemical synthesis of peptides are well known in the art and may be found in general texts in the area such as Duchas H and Penny C., *Bioorganic Chemistry*, (1981) Springer-Verlag, N.Y. at pages 54–92. For example, peptides may be synthesized by solid phase methodology utilizing fluorenylmethyoxycarbonyl chemistry on a Miligram/Biosearch 9600 peptide synthesizer. Butoxycarbonyl (BOC) amino acids and other reagents are commercial available from Advanced Chemtech, Louisville, K.Y. and Milipore Colo., Marlboro, Mass. and other chemical supply houses. Sequential batch chemistry using double couple protocols can be applied to starting p-methylbenzyl hydroamine resins for the production of C-terminal carboxyamides. For the production of C-terminal acids, the corresponding PAM resin is used. Asparagine, glutamine and arginine are coupled using free formed hydroxybenzotriazyl esters. Side chain protecting groups may be used to form amino acids such as arginine, aspartic acid, glutamic acid, serine, threonine, and tyrosine. BOC de-protection may be accomplished with trifluoroacetic acid and methylene chloride. Following completion of synthesis, the peptides may be deprotected and cleaved from the resin with hydrogen fluoride (HF) containing 10% metacresol. Cleavage of the side chain protecting groups and of the peptide from the resin is carried out at 0° C. or below for 30 minutes, followed by 30 minutes at 0° C. After removal of the HF, the peptide/resin is washed with ether and the peptide extracted with glacial acetic acid and lyophilized.

Lyophilized crude peptide can be further isolated and purified using column chromatography methods, such as high pressure liquid chromatography. Isolation of the peptides can be accomplished using reverse phase HPLC on a C-18 column with an elution gradient of 0–60% acetylnitrile with 0.1% trifluoroacetic acid in water. Isolated peptides can also then be subjected to gel filtration using a column such as a Sephadex G-25 column. The purity of the peptides can be verified by reverse phase HPLC. Confirmation of the amino acid sequence of the peptides can be obtained standard amino acid analysis.

Once the peptides have been synthesized and isolated, they can be further modified by the formation of dimers, cyclic compounds and by conjugation to carrier molecules. Formation of dimers can be preferably accomplished when peptides having one cysteine residue are present at a concentration of about 3 mM and are stirred under oxidizing conditions. Formation of cyclic peptides can be accomplished using standard methods as described by Rustici et al., *Science* 259:361 (1993). Peptides having at least 2 cysteine residues can be cyclized by air oxidation with continuous stirring under conditions which favor the formation of intrachain disulfide bridges (i.e., concentration of 0.1 mg/ml (1 uM) or less). Cyclic peptides can also be purified by reverse phase HPLC with a linear methanol in water gradient of 20–80% and identified as a single peak that elutes earlier than the linear peptide. Dimers can also be isolated by HPLC and elute as a single peak later than the linear peptide. Oxidation of the thiol groups of cysteine residues can be ascertained by use of Ellman's reagent.

The peptides can also be conjugated to larger molecular weight carrier proteins such as keyhole limpet hemocyanin (KLH) or bovine serum albumin (BSA) or ovalbumin. Peptides can be conjugated to the carrier proteins using a standard method such as activation of the carrier molecule with a heterobifunctional sulfosuccinimidyl 4-(n-maleimidomethyl) cyclohexane-1-carboxylate reagent. Crosslinking of activated carrier to a peptide can occur by reaction of the maleimide group of the carrier with the sulfhydryl group of a peptide containing a cysteine residue. Conjugates can be separated from free peptide through the use of gel filtration column chromatography.

For large scale preparation of the peptides derived from or corresponding to sequences of the B/PI, production by recombinant DNA technology methods may be desirable. Standard recombinant DNA technology methods are known to those of skill in the art and are described in texts such as *A Guide to Molecule Cloning: A Laboratory Manual* by Maniatis et al., Cold Spring Harbor, N.Y. (1989).

The general scheme for preparation of recombinant peptides derived from B/PI is as follows: (1) obtain a DNA sequence coding for the peptide either from a naturally occurring sequence, a cDNA sequence, or a synthetic or semi-synthetic sequence coding for B/PI; (2) modifying the DNA sequence to code for a modified peptide like, for example, including an N- and/or C-terminal cysteine; (3) amplifying the DNA sequence and combining the sequence with transcriptional and translational control regions functional in a host cell; and (4) transforming a host cell and isolating the recombinant peptide produced therein.

The DNA sequence coding for a peptide derived from or corresponding to amino acid sequences of B/PI can be wholly synthetic or the modification of a native DNA or cDNA sequence coding for B/PI. A DNA or cDNA sequence that encodes native B/PI is shown in FIG. 4 or FIG. 8 and can be used as starting material to obtain a DNA sequence coding for a biologically active peptide derived from B/PI.

A synthetic sequence coding for a biologically active peptide of B/PI can be constructed by techniques well known in the art and as described by Brown et al., *Methods in Enzymology*, 68:109–151 (1979). For example, DNA sequences encoding a peptide having the amino acid sequence of residues 82–108 of B/PI can be designed taking into account the known codon usage for a particular host cell and by reference to the DNA or cDNA sequence coding for B/PI at those amino acid residues. It will be understood by those of skill in the art that owing to the degeneracy of the genetic code, a sizeable yet definite number of DNA sequences can be constructed to code for peptides having an amino acid sequence derived from or corresponding to regions of B/PI. Once designed, the sequence can be synthesized using commercially available DNA synthetic technology.

Alternatively, a DNA sequence encoding a peptide derived from B/PI can be obtained from a DNA or CDNA sequence coding for B/PI by subcloning a restriction fragment including a DNA sequence coding for the desired peptide. The recognition sequences for restriction enzymes are known to those of skill in the art and based upon the DNA sequence of FIG. 4, one of skill in the art can select the restriction enzymes that will result in a fragment including a DNA sequence coding for the desired peptide.

In another method, a DNA sequence coding for a peptide derived from B/PI can be obtained by amplification of a selected sequence using polymerase chain reaction (PCR). Primers can be prepared which hybridize to the 5' and 3' ends of the region of the DNA sequence coding for the desired peptide. Primers can be designed using known principles and synthesized using automated synthesis. Examples of several primers are shown in FIG. 4. Amplification and isolation of the desired DNA sequence can be accomplished using standard PCR techniques.

Once a DNA sequence encoding the desired peptide is obtained, it can be modified by standard methods. For example, DNA sequences encoding various restriction sites can be added onto either or both the 5' and 3' ends of the sequence to provide for ease of cloning. Other modifications include adding DNA coding sequence for additional N-terminal or C-terminal amino acids such as a DNA sequence coding for cysteine or methionine or for stop codons. These modifications can be readily accomplished with PCR and appropriately designed primers. DNA sequences including changes such as amino acid substitution or deletions can be prepared either by automated synthesis, by site specific mutagenesis, or by combining a synthetic DNA sequence coding for the modified portion of the peptide with a cDNA or DNA sequence for the peptide.

Once the DNA sequence coding for the desired peptide is obtained, it can be inserted into any one of the many appropriate and commercially available DNA expression vectors through the use of appropriate restriction endonucleases. See generally Maniatis, cited supra. The particular endonucleases involved will be dictated by restriction endonuclease sites in the expression vector. The DNA sequences coding for the peptide are inserted in frame and operably linked to transcriptional and translational control regions which are present in the vector and are functional in the host cell. Appropriate transcriptional and translational control regions are known to those of skill in the art and are present in publicly available expression vectors. The DNA sequence coding for the peptide can be inserted into a system that results in expression of fusion protein including a protein such as B-galactosidase.

Figure 7:
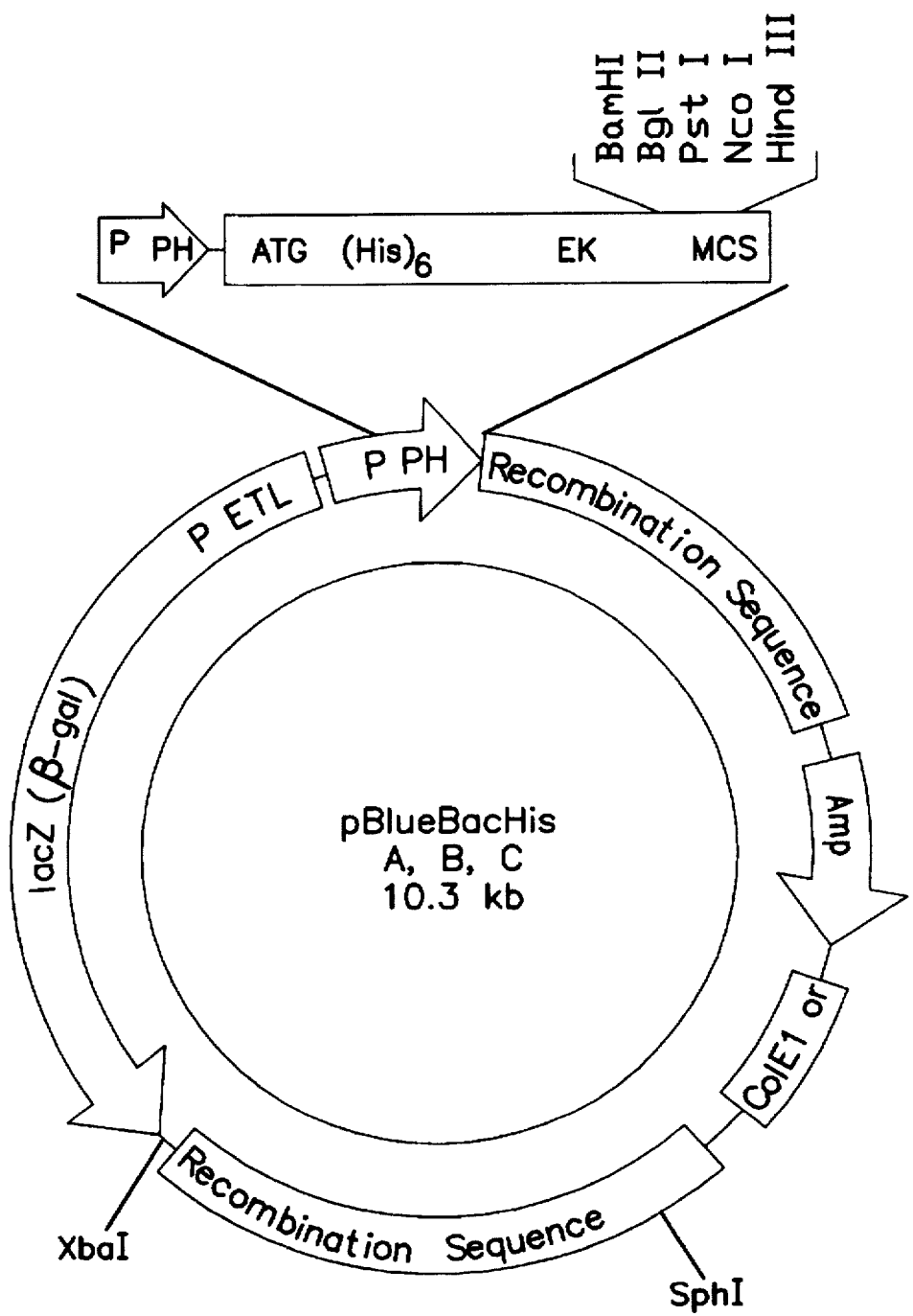
FIG. 7 is a restriction map of the Bluebac His III vector.

A variety of expression vectors useful for transforming prokaryotic and eukaryotic cells are well known in the art. See the *Promega Biological Research Products* catalog (1992). An expression system that is especially preferred is a baculovirus transfer vectors pVC1393 or Bluebac His III vector (Invitrogen Corp., San Diego, Calif.). Co-infection of insect cells with the recombinant transfer vector including a DNA sequence coding for a peptide derived from B/PI and the wild type baculovirus results in the expression of a recombinant product such as B/PI or peptides derived from B/PI under the control of the promoter of the polyhedron gene. A partial restriction map of the Bluebac His III vector is shown in FIG. 7.

Recombinant virus can be identified by formation of visibly different plaque morphology. Cells producing recombinant virus can also be detected by expression of a B-galactosidase fusion protein. Plaques with the highest level of expression of the peptide can also be detected immunologically or by hybridization to a probe that is specific for the DNA sequence coding for the desired peptide. Selected recombinant viruses can be plaque purified and can be amplified for large scale production of the peptide in SF9 insect cells. The recombinant peptides can be isolated from insect cell lysates, and peptides can be isolated by immunoaffinity chromatography and/or reverse phase HPLC.

D. Methods for Treating a Bacterial Infection

The invention also provides methods for treating a bacterial infection. The method involves a step of administering to an animal an amount of pharmaceutical composition effective to inhibit the bacterial infection. The pharmaceutical composition comprises a bactericidal peptide having an amino acid sequence derived from or corresponding a peptide from B/PI and preferably includes the amino acid sequence KWKAQKRFLK (SEQ ID NO:6). The bactericidal protein is in an admixture with a pharmaceutically acceptable carrier and can be administered in a variety of ways to effectively treat bacterial infections.

A bactericidal peptide is derived from or corresponds from a peptide from B/PI. The peptide can kill bacteria such as *Pseudomonas spp., E. coli B*, and Staphylococcus. The bactericidal peptide preferably is about 10–100 amino acids long, and more preferably about 10–40 amino acids long. The peptide preferably includes the amino acid sequence KWKAQKRFLK (SEQ ID NO:6) and can be linear cyclic, dimer or hybrid form of the peptide. The peptide also is preferably soluble in water or solvent such as DMSO has a half-life in vivo of about 0.5 hours to about 5 hours. The especially preferred peptides are those including the amino acid sequence:

CKWKAQKRFLKC (SEQ ID NO:25);

CNANIKISGKWKAQKRFLKMSGNFDLSIC (SEQ ID NO:28); and

CKISGKWKAQKRFLKMSGNFC (SEQ ID NO:29) in linear or cyclic form.

The effective amount of a peptide for treating a bacterial infection will depend on the bacterial infection, the location of the infection and the peptide. An effective amount of the peptide is that amount that diminishes the number of bacteria in the animal and that diminishes the symptoms associated with bacterial infection such as fever and pain. The effective amount of a peptide can be determined by standard dose response methods in vitro and an amount of peptide that is effective to kill at least 50–100% of the bacteria ($LD_{50}$) and more preferably about 60–100% of the bacteria would be considered an effective amount.

Alternatively an effective amount of the peptide for treating a bacterial infection can be determined in an animal system such as a mouse. Acute peritonitis can be induced in mice such as outbred Swiss webster mice by intraperitoneal injection with bacteria such as *Pseudomonas aeruginosa* as described by Dunn et al., *Surgery*, 98:283 (1985); Cody et al., *Internal Surgical Research*, 52:315 (1992). Different amounts of the peptide can injected at one hour intravenously prior to the injection of the bacteria. The percentage of viable bacteria in blood, spleen and liver can be determined in the presence and absence of the peptide or other antibiotics. While not meant to limit the invention, it is believed that bactericidal peptide could also enhance the effectiveness of other antibiotics as erythromycin by increasing the uptake of the antibiotics by the bacteria.

The bactericidal peptide can be used to treat infections with *Pseudomonas spp., E. coli* strains, other gram-negative bacteria such as Salmonella, *Proteus mirabilis* and gram positive *S.aureus*. The bactericidal peptide is preferably used to treat infections with *Pseudomonas spp.*, both rough and smooth strains, mucoid and nonmucoid strains of Pseudomonas. The infection can be systemic or surface infection, such as on the skin or mucosal membranes.

The bactericidal peptide can be combined with a variety of physiological acceptable carriers, diluents or excipients known to those of skill in the art. For example, for parenteral administration, isotonic saline is preferred. For topical administration a cream, including a carrier such as dimethylsulfoxide (DMSO) is preferred. Other suitable carriers include alcohol, phosphate buffered saline and other balanced salt solutions.

The peptide can be administered in a variety of ways, including intravenously, topically, orally and intramuscularly to a variety of animals, including humans, mice and rabbits. The peptides can be administered as a single dose or in multiple doses. Preferably the dose is an effective amount as determined by the standard methods described herein and includes about 1 microgram to about 1,000 micrograms per treatment, more preferably about 50 to about 250 micrograms per treatment. E. Method for Treating Endotoxin Shock The invention also provides a method for treating endotoxin shock. The steps of the method involve administering a pharmaceutical composition to an animal in an amount sufficient to diminish the symptoms of endotoxin shock, including release of TNFα into the blood stream, fever, decrease in blood pressure and intravascular coagulation. The pharmaceutical composition includes a peptide derived from or corresponding to peptides from B/PI and can neutralize endotoxin. The endotoxin neutralizing peptide is in admixture with a pharmaceutically acceptable carrier and can be administered in a variety of ways.

An endotoxin neutralizing peptide derived from or corresponding to a peptide B/PI can neutralize endotoxin as determined by an in vitro test such as LAL or chromogenic LAL test, preferably at a concentration of about $10^{-5}$ to $10^{-8}$M. The endotoxin neutralizing peptide is about 10–100 amino acids long and preferably 10–40 amino acids long. The peptide preferably also is bactericidal and includes the amino acid sequence KWKAQKRFLK (SEQ ID NO:6) and can be a linear, cyclic, dimer or hybrid form of the peptide. The peptide is also preferably soluble in water and/or a solvent such as DMSO and has half-life in vivo of about 0.5 to 5 hours. The especially preferred peptides are those including the following amino acids sequence:

CNANIKISGKWKAQKRFLKMSGNFDLSIC (SEQ ID NO:28);

CKISGKWKAQKRFLKMSGNFC (SEQ ID NO:29); and

CKWKAQKRFLKC (SEQ ID NO:25)

in linear or cyclic form.

The effective amount of a peptide for treating endotoxin shock can be determined by in vitro methods to determine the amount that will neutralize endotoxin. An effective amount of endotoxin neutralizing peptide is that amount that decreases the symptoms of endotoxin shock such as fever, shock and TNFa release. The amount of endotoxin neutralizing peptide that will neutralize about 50% ($ID_{50}$) of $10^{-6}$ to $10^{-9}$gm of endotoxin can be determined using the LAL or the chromogenic LAL assay for endotoxin neutralization. The endotoxin neutralizing peptide preferably neutralizes about 50–100% of the endotoxin neutralizing activity and more preferably about 90–100%.

Alternatively, an effective amount of an endotoxin neutralizing peptide can be determined by measuring the effect of differing amounts of a endotoxin neutralizing peptide on the ability of lipopolysaccharide (LPS) to stimulate release of tumor necrosis factor alpha (TNF) from a macrophage cell line. A macrophage cell line can be incubated with LPS in the presence or absence of different amounts of endotoxin neutralizing peptide. Production of TNFa can be assayed as described by Mossman et al., *Immunological Methods*, 65:55 (1983). An inhibitory dose 50 ($ID_{50}$) can be calculated according to standard methods.

Another option for determining the effective amount of a endotoxin neutralizing peptide is to determine the amount of endotoxin neutralizing peptide that will inhibit endotoxin mediated pyrogenicity in rabbits. Samples of endotoxin and differing amounts of peptides can be mixed and incubated for about 30 minutes. The mixtures are then tested for the ability to stimulate pyrogenicity by intravenous injection into rabbits. Temperature of the rabbits is monitored over time. An inhibititory dose ($ID_{50}$) can also be calculated based upon these results by standard methods.

The endotoxin neutralizing peptide can be used to treat animals infected with gram-negative bacteria systemically and that exhibit symptoms of endotoxin shock such as fever, shock and TNFA release. The animals are typically infected with one or more gram-negative bacteria such as Pseudomonas spp. rough strains of *E. coli*, encapsulated *E. coli* and smooth strain *E. coli*. The endotoxin neutralizing peptide can be combined with other agents that are known and used by those skilled in the art to treat endotoxin shock.

The endotoxin neutralizing peptide can be combined with a variety of physiologically acceptable carriers, diluents or excipients known to those skilled in the art. For example, carriers, include isotonic saline, phosphate buffered saline, and other balanced salt solution that may include plasma expanders. The peptide can be administered in a variety of ways including intravenously, topically, orally and intramuscularly to a variety of animals including humans, mice and rabbits. The peptides can be administered in a single dose or multiple doses. Preferably the dose is an effective amount as determined by the methods described herein and includes about 1 ug to 1,000 ug per treatment and more preferably about 50 to 250 ugms per treatment.

F. Prosthetic Devices

The invention also provides for prosthetic or implantable devices that are coated with or to which a bactericidal peptide is attached. The bactericidal peptide is attached or coated on a surface of the prosthetic or implantable device in an amount effective to inhibit growth of bacteria on the surface. The bactericidal peptide is derived from or corresponds to a peptide of B/PI and preferably includes the amino acid sequence KWKAQKRFLK (SEQ ID NO:6). The bactericidal peptide can be attached to a linking compound such as a carrier protein and then attached to the surface of prosthetic or implantable device.

A bactericidal peptide for attachment to prosthetic devices is preferably about 10–100 amino acids long and has been modified by the addition of a cysteine or glycine residue that can serve as a site of attachment to the prosthetic device. The peptide also preferably also includes the peptide sequence KWKAQKRFLK (SEQ ID NO:6) and can be a linear, cyclic, dimer or hybrid form of the peptide. The especially preferred peptides are:

CKWKAQKRFLKC (SEQ ID NO:25);

CNANIKISGKWKAQKRFLKMSGNFDLSIC (SEQ ID NO:28); and

CKISGKWKAQKRFLKMSGNFC (SEQ ID NO:29) in a linear or cyclic form.

The amount of the bactericidal peptide effective to inhibit growth on the surface can be determined by coating a surface such as an agar plate with different amounts of a bacteria and overlaying the surface with a lawn of bacteria such as *Pseudomonas spp*. The amount of a bactericidal peptide that results in a 50–100% inhibition of the bacteria and more preferably 90–100% an inhibition of growth on the surface is an effective amount.

Types of prosthetic or implantable devices include catheters, I.V. tubing, drug-delivery pumps, cardiac pacemakers, bone replacement prosthetics and shunts used in the brain. Hydrogels such as polymethylolmethacrylamide (PMMA) can also be used for implants in the body. Devices intended for cardiac insertion include heart valves and left ventricular assist devices formed from synthetic resins such as polyurethane elastomers or from vulcanized polyolefin rubbers. As the device remains in the body, the chance of developing infection with hospital related microorganisms such as P. cepacia increases. Coating implantable or prosthetic devices with a bactericidal peptide can drastically reduce the rate of infection associated with the introduction of devices into the body.

Attachment of the peptide can be proceed by standard methods and will depend on the nature of the surface of the prosthetic device. Attachment of the peptide may require the presence of linking agent that can link the peptide to the surface. For a review of synthetic resins and biomaterials in prosthetic devices. See *Chem. & Eng. News* (Apr. 14, 1986) at pages 30–48. Preferably the attachment to the surface is a covalent attachment and does not destroy the biological activity of the peptide. Preferably the attachment is through a cysteine residue at the N and/or C-terminal end of the peptide.

Once coated the prosthetic devices can be introduced into an animal such as human.

EXAMPLE 1

Generation of Peptides from Human Neutrophil Granule Bactericidal Protein

Some short (about 9 to 35 amino acids) hydrophilic peptides based on the structure of the 55 kD bactericidal protein B/PI from human neutrophil granules were identified from the hydropathy plot of predicted 456 amino acid sequence of B/PI (Table 1). The predicted amino acid sequence was obtained from the nucleotide sequence of a cDNA clone of B/PI, as shown in FIG. 4 or FIG. 8. These peptides and other related peptides were synthesized by automated methods. The peptides prepared by automated synthesis as described below were optionally coupled to keyhole limpet hemocyanin or ovalbumin protein carriers.

Peptide Preparation

Peptides were synthesized at the University of Minnesota Microchemical Facility using a Millgren/Biosearch 9600 peptide synthesizer. All peptides were solid-phase synthesized by use of fluorenylmethoxycarbonyl chemistry. The profile of cleaved peptide was obtained by analytical high performance liquid chromatography (HPLC) (Model HP1090 from Hewlett Packard). When necessary, lyophilized crude peptides were purified by preparative reverse-phase HPLC on a C18 column with an elution gradient of 0–60% acetonitrile with 0.1% trifluoroacetic acid in water. Crude and pure peptides were subjected to gel filtration using a 1×9 cm Sephadex G25 column and pyrogen-free saline buffered with 0.008M citrate phosphate buffer, pH 7.0, as elution buffer and used to confirm results obtained at every step of the study. The purity and composition of the peptides were verified by HPLC (Beckman Model 6300). Analysis of amino acid composition of the peptides were obtained from hydrolysates prepared by treating the peptides under argon in 6 N HCl for 24 hours at 110° C. The thiol groups of all peptides containing a cysteine residue were fully reduced as ascertained with Ellman's reagent using reduced glutathione as a standard.

The peptides synthesized are shown in Table 2.

TABLE 2

| Peptide Number | Code | Sequence |
|---|---|---|
| 1 | Signal | mrenmargpc (SEQ ID NO:13) |
| 2 | C#90-99 | ckwkaqkrflk (SEQ ID NO:7) |
| 3 | C#227-236 | cefysenhhnp(g) (SEQ ID NO:17) |
| 4 | C#418-427 | cneklqkgfpl (SEQ ID NO:18) |
| 5 | #90-99 | kwkaqkrflk (SEQ ID NO:6) |
| 6a | #27-37 | kelkrikipdy (SEQ ID NO:14) |
| 6b | C#27-37 | ckelkrikipdy (SEQ ID NO:41) |
| 7a | #160-170 | kkiesalrnkm (SEQ ID NO:16) |
| 7b | C#160-170 | ckkiesalrnkm (SEQ ID NO:42) |
| 8a | #86-89 | kisgkwkaqkrflk (SEQ ID NO:9) |
| 8b | C#86-99 | ckisgkwkaqkrflk (SEQ ID NO:10) |
| dimer 8b | | ckisgkwkaqkrflk<br>|<br>ckisgkwkaqkrflk |
| 9a | #90-102 | kwkaqkrflkmsg (SEQ ID NO:8) |
| 9b | C#90-102 | ckwkaqkrflkmsg (SEQ ID NO:27) |
| 10a | #118-127 | klgsnptsgk (SEQ ID NO:15) |
| 10b | C#118-127 | cklgsnptsgk (SEQ ID NO:43) |
| 11 | F1 #1-26 | vnpgvvvrisqkgkldyasqqgtaalq (SEQ ID NO:21) |
| 12 | F2 #38-62 | sdsflkikhlgkghysfysmdirefq (SEQ ID NO:32) |
| 13 | F3 #63-89 | lpssqismvpnvglkfsisnanikisg (SEQ ID NO:44) |
| 14 | F4 | msgnfdlsiegmsisadl (SEQ ID NO:45) |
| 15 | F5 | ptitcsscsshinsvhvhiskskvgwliqlfh (SEQ ID NO:46) |
| 16 | F6 | mnsqvcekvtnsvssklqpyfqtlpvmtki (SEQ ID NO:47) |
| 17 | CHybrid | cefysenhhnpkwkaqkrflk (SEQ ID NO:12) |
| dimer 17 | | cefysenhhnpkwkaqkrflk<br>|<br>cefysenhhnpkwkaqkrflk |
| 18 | Hybrid | efysenhhnpkwkaqkrflk (SEQ ID NO:11) |
| 19 | rand.90-99 | wkkfkqralk (SEQ ID NO:35) |
| 20a | | ckwkaqkrflkc (SEQ ID NO:25) |
| cyclic 20a | | ckwkaqkrflkc (SEQ ID NO:40) |
| 20b | #90-99c | kwkaqkrflkc (SEQ ID NO:26) |
| 21 | rand.90-99 | kkkwfrlakq (SEQ ID NO:36) |
| 22 | #82-#108 | nanikisgkwkaqkrflkmsgnfdlsi (SEQ ID NO:20) |
| 23 | C#82-108C | cnanikisgkwkaqkrflkmsgnfdlsic (SEQ ID NO:28) |
| cyclic 23 | | cnanikisgkwkaqkrflkmsgnfdlsic (SEQ ID NO:33) |
| 24 | Rustici#6 | iktkkflkkt (SEQ ID NO:48) |
| 25 | Rustici#2 | ktkckflkkc (SEQ ID NO:49) |
| cyclic | | cktkckflkkc (SEQ ID NO:50) |
| 26 | (peptide 19) wk→kw | kwkfkqralk (SEQ ID NO:24) |
| 27 | #93 (peptide 21) w→f | kkkffrlakq (SEQ ID NO:38) |
| 28 | #93 (peptide 21) w→a | kkkafrlakq (SEQ ID NO:39) |
| 29 | #100-109 | msgnfdlsie (SEQ ID NO:51) |
| 30 | #80-89 | isnanikisg (SEQ ID NO:52) |
| 31 | #83-92 | anikisgkwk (SEQ ID NO:53) |

TABLE 2-continued

| Peptide Number | Code | Sequence |
|---|---|---|
| 32 | #86-95 | kisgkwkaqk (SEQ ID NO:54) |
| 33 | #94-103 | qkrflkmsgn (SEQ ID NO:55) |
| 34 | #97-106 | flkmsgnfdl (SEQ ID NO:56) |
| 34b | C#97-106C | cflkmsgnfdlc (SEQ ID NO:57) |
| 35 | #86-104 | kisgkwkaqkrflkmsgnf (SEQ ID NO:19) |
| 36 | C#86-104C | ckisgkwkaqkrflkmsgnfc (SEQ ID NO:29) |
|  | cyclic 36 | ckisgkwkaqkrflkmsgnfc (SEQ ID NO:34) |
| 37 | 82-92 | nanikisgkwk (SEQ ID NO:58) |

Peptides corresponding to different portions of the amino terminal end of the B/PI molecule were synthesized and modified in various ways. Peptides synthesized containing an N-terminal cysteine are given the designation C before the amino acid numbers. Peptides synthesized with N- and C-terminal cysteines were designated with a C before and after the amino acid numbers. Peptides can be synthesized with an internal cysteine residue. Peptides with a C-terminal cysteine have a C after the amino acid numbers. Peptides with N- and C-terminal cysteines can be cyclized as described below. Some of the peptides were dimerized as described below. Peptides containing the same amino acids as peptide #90-99 were generated randomly. Those peptides are designated rand., as shown in peptides 19, 21, 26, 27, or 28. The randomly generated peptide 21 was modified by specific replacement of tryptophane (W) at residue 93 with phenylalanine (F) (peptide 27) or alanine (A) (peptide 28). The randomly generated peptide 19 was modified at amino acid residues #90 and #91 for WK to KW (peptide 26).

Once synthesized and purified, the peptides were assayed for biological activity.

Method for Preparing Cyclic Peptides

Peptides (0.1 mg/ml (1 uM) pH 7.0) were cyclized by air oxidation with continuous stirring for 72 hours, under conditions which favor intrachain disulfide bridges. Peptides were purified by reversed-phase HPLC with a linear methanol in water gradient of 20 to 80%. A cyclic peptide eluted as a single peak earlier than the corresponding linear peptide. Amino acid composition of the peptides was confirmed by Pico-Tag analysis (Waters). Quantitation of amino groups in the peptides was as described. Mannion et al., cited supra. Oxidation of the thiol groups of cysteine residues was ascertained by Ellman's reagent. Cyclic peptides were assayed for biological activity.

Method for preparing Peptide Dimers

For preparation a dimer, 3 mM of a peptide having one cysteine residue in pyrogen free saline was dimerized by air oxidation by continuous stirring for 72 hours. Dimers were isolated by reverse phase HPLC with a linear methanol in water gradient of 20–80%. Dimers eluted as a single peak at a time later than the corresponding monomers.

Conjugation of Peptides to Protein Carriers

Peptides were conjugated to Keyhole Limpet hemocyanin or ovalbumin carrier proteins which had been activated with the heterobifunctional sulfosuccinimidyl 4-(N-maleimidomethyl)cyclohexane-1-carboxylate reagent. Cross-linking of activated carrier to peptide was due to the reaction of the maleimide group of the carrier with the sulfhydryl group of the peptide and according to the manufacturer's instructions (monograph #77108, Pierce Chemical Company, Rockford, Ill.). Conjugates were separated from free peptide with a 1×9 cm Sephadex G25 column, rather than the column provided by the manufacturer. Conjugates and unconjugated protein carriers were hydrolyzed and the amino acid composition determined as described above. Using the amino acid composition of carrier compared with conjugate, the stoichiometry of peptide to carrier and the molecular mass of each conjugate was determined. Assuming a molecular mass of 70 kD for KLH and of 45 kD for ovalbumin, the molar concentration of peptide in each conjugate was calculated by the difference. Peptides conjugated to protein carriers were also assayed for biological activity.

Purification of B/PI

B/PI was purified in three column chromatography steps as previously described. Wasiluk et al., Infection and Immunology, 59:4193 (1991). In the final step, the sample was applied to a 1×180 cm molecular sieving column of Toyopearl HW55S (TosoHaas, Philadelphia, Pa.) which had been equilibrated with 0.05M glycine buffer, containing 0.5M NaCl (pH 2.5). Protein concentration was determined according to Hartree, Anal. Biochem., 48:422–427 (1972). Purity was confirmed by visualization of a SDS polyacrylamide gel following electrophoresis of 1 μg of purified B/PI protein and silver staining of the gel, also as previously described.

EXAMPLE 2

Assay of the Synthetically Produced Peptides for Bactericidal Activity

The synthetically produced peptides were assayed for bactericidal activity against Pseudomonas aeruginosa, type 1, P. cepacia ATCC 25608, E. coli B, and Staphylococcus aureus 502A by standard methods.

Bacteria

Pseudomonas aeruginosa type 1 is a clinical isolate maintained in the laboratory since 1972. The isolate remains a smooth strain and was serotyped by the scheme of Homma. Homma, Jpn. J. Exp. Med., 46:329 (1976). A rough strain E. coli B and S. aureus 502A were obtained from Paul Quie, University of Minnesota. The characteristics of the S. aureus strain have been described in Shinefield et al., Amer. J. Dis. Chil., 105:646 (1963). Pseudomonas cepacia ATCC 25608 was purchased from the American Type Culture Collection in 1980. S. aureus and E. coli were maintained on nutrient agar plates and the Pseudomonas strains were maintained on blood agar plates.

Bactericidal Assay

Pyrogen-free solutions were used throughout this assay and all methods which follow. Log phase bacteria were prepared from a culture in brain heart infusion broth as previously described except that bacteria were washed and resuspended in saline with adjustment to an optical density at 650 nm which would yield $3 \times 10^8$ CFU/ml. Bacteria were then diluted 1:10 in 0.08M citrate phosphate buffer, pH 5.6 or pH 7.0, for use in the assay. S. aureus rapidly lost viability in the pH 5.6 buffer and was studied only at pH 7.0. Bactericidal activity was determined by dose response and where an LD50 is indicated, it was determined by linear regression.

The bactericidal activity of three of the synthetic peptides against four different bacteria was compared with the 55 kD B/PI protein. The results are shown in Table 3.

TABLE 3

Bactericidal Activity of B/PI and of Synthetic Peptides Related to B/PI

| | % Killing of 5 × 10⁶ Bacteria | | | | | | | |
|---|---|---|---|---|---|---|---|---|
| | B/PI $(4.1 \times 10^{-9}M)$ | | C#90-99 $(1.5 \times 10^{-6}M)$ | | C#227-236 $(1.2 \times 10^{-4}M)$ | | C#418-427 $(1.2 \times 10^{-4}M)$ | |
| Bacteria | pH 5.6 | pH 7.0 | pH 5.6 | pH 7.0 | pH 5.6 | pH 7.0 | pH 5.6 | pH 7.0 |
| P. aeruginosa | 50 ± 5 | 35 ± 3 | 83 ± 13 | 83 ± 15 | 0 | 0 | 0 | 0 |
| P. cepacia | 0 | 0[b] | 0 | 0[c] | 0 | 0 | 0 | 0 |
| E. coli | 35 ± 4 | 25 ± 5 | 0 | 0[d] | 0 | 0 | 0 | 0 |
| S. aureus | — | 0[b] | — | 0[e] | — | 0 | — | 0 |

*Values shown are the mean ± one standard error for three experiments
[b]P. cepacia and S. aureus were not killed at a concentration 20-fold higher (approximately 5 µg protein/ml)
[c]78% of P. cepacia were killed at $1.5 \times 10^{-5}M$, pH 7.0, and 80% at pH 5.6
[d]90% of E. coli were killed at $1.5 \times 10^{-5}M$, pH 7.0, and 98% at pH 5.6
[e]95% of S. aureus were killed at $3 \times 10^{-5}M$, pH 7.0

The bactericidal activity of the C#90-99 peptide towards four different bacteria is compared in Table 3 with the activity of two other peptides, C#227-236 and C#418-427 of the mature B/PI molecule. The latter two peptides were synthesized with an amino-terminal cysteine for the comparison with C#90-99 and so that they could be coupled to protein carrier molecules through the thiol group. The C#227-236 sequence occurs at the halfway point of the molecule of B/PI. This peptide was synthesized with a carboxy-terminal glycine to facilitate cleavage from the resin after synthesis of the peptide.

The C#227-236 and C#418-427 peptides were not bactericidal for any of the four bacteria shown in Table 3. The highest dose of these peptides tested was $1.2 \times 10^{-4}$. As shown in Table 3, B/PI was equally bactericidal toward P. aeruginosa and a rough strain E. coli at $4.1 \times 10^{-9}M$ (approximately 0.2 µg protein/ml). There was a small but reproducible loss of activity at pH 7.0, compared to pH 5.6. P. cepacia and S. aureus resisted bactericidal activity at $9.1 \times 10^{-8}M$ of B/PI, or approximately a 20-fold higher protein concentration than that which killed P. aeruginosa. By comparison with B/PI, the C#90-99 peptide killed P. aeruginosa when tested at $1.5 \times 10^{-6}M$ (2.1 µg of peptide/ml). E. coli and P. cepacia were killed at a peptide concentration of C#90-99 which was 10 times higher than the peptide concentration which killed P. aeruginosa. Killing of S. aureus by C#90-99 occurred at 20 times the concentration which killed P. aeruginosa.

The hydrophilic peptides #27-37, #118-127 and #160-170 shown in Table 2 were not bactericidal at $1.2 \times 10^{-4}M$ for any of the bacteria of this study (data not shown). A peptide corresponding to the first 10 amino acids of the signal sequence for B/PI also was not bactericidal and data is not shown for studies of this peptide.

The dose response of 5×10⁶ CFU of P. aeruginosa to peptides C#90-99 —#90-99, and B/PI was determined and the results are shown in FIG. 1. The bactericidal activity of the #90-99 peptide toward P. aeruginosa was linear with dose (FIG. 1) and is compared in the figure with the dose response of the most active of the bactericidal peptides, which was the #90-99 peptide with an added cysteine (C) at the amino terminus (C#90-99). The LD₅₀ of C#90-99 for P. aeruginosa was achieved at a 11.8 times lower peptide concentration than the LD₅₀ of peptide #90-99 ($8.2 \times 10^{-6}M$) and 37.7 times higher than the LD₅₀ for B/PI ($3.4 \times 10^{-9}M$). When compared to C#90-99, approximately 10 to 12-fold more of the peptide without the added cysteine (#90-99) was required for equal killing of P. aeruginosa. The #90-99 peptides were equally active towards two mucoid variants of P. aeruginosa and ATCC strain 27312 of P. aeruginosa (not shown).

Bactericidal activity of peptides was tested for killing of 5×10⁶ bacteria at pH 5.6. Peptides containing the amino acid residues 90-99 of B/PI were tested as well as two hybrid peptides. The hybrid peptides have the sequence shown in Table 2 for peptide 18 (Hybrid) and peptide 17 (CHybrid). The Hybrid peptide (18) represents a combination of the amino acid sequence for peptide #90-99 and #227-236. The CHybrid (17) has the same sequence as the hybrid peptide except it has an N-terminal cysteine. The peptides were tested for bactericidal activity and the results are shown in Table 4. When rough strain E. coli were tested at pH 5.6 with $3 \times 10^{-5}M$ of #90-99, 31% of 5×10⁶ bacteria were killed (Table 4). The #90-99 peptide concentration required to kill P. cepacia at pH 5.6 and S. aureus at pH 7.0 was 5 times higher than the effective concentration of C#90-99 (not shown).

TABLE 4

Bactericidal Activity of Synthetic Peptides at pH 5.6

| | % Killing of 5 × 10⁶ Bacteria (Molar Concentration) | |
|---|---|---|
| Synthetic Peptides | P. aeruginosa | E. coli B |
| C#90-99 | 83 ± 13 ($1.5 \times 10^{-6}M$) | 98 ± 3 ($1.5 \times 10^{-5}M$) |
| #90-99* | 75 ± 0 ($1.5 \times 10^{-5}M$) | 31 ± 3 ($3.0 \times 10^{-5}M$) |
| #86-99 | 79 ± 3 ($6.0 \times 10^{-6}M$) | 90 ± 1 ($3.0 \times 10^{-5}M$) |
| C#86-99 | 90 ± 5 ($3.0 \times 10^{-6}M$) | 91 ($1.5 \times 10^{-5}M$) |
| #90-102 | 67 ± 4 ($6.0 \times 10^{-6}M$) | 77 ± 6 ($3.0 \times 10^{-5}M$) |
| Hybrid | 79 ± 5 ($3.0 \times 10^{-6}M$) | 72 ($6.0 \times 10^{-5}M$) |
| CHybrid | 74 ± 3 ($3.0 \times 10^{-6}M$) | 71 ($3.0 \times 10^{-5}M$) |
| B/PI | 87 ± 8 ($5.5 \times 10^{-9}M$) | 71 ($5.5 \times 10^{-9}M$) |

*n = 6

The molar dose of peptides #86-99 and #90-102 required to kill P. aeruginosa was 2.5 times lower than the effective dose of the #90-99 peptide (Table 4, FIG. 1). At pH 5.6, neither the #90-102 nor the #86-99 peptide were substantially improved over the bactericidal activity of peptide #90-99 toward E. coli (Table 4).

At pH 5.6, the CHybrid molecule killed 74% of 5×10⁶ P. aeruginosa cells at $3 \times 10^{-6}M$. This is a concentration of CHybrid 5-fold lower than the concentration of #90-99 required to kill 75% of the bacteria (Table 4, FIG. 1) and two times higher than the concentration of C#90-99 which killed 83% of the bacteria (Table 4, Table 3). The Hybrid molecule killed 79% of the P. aeruginosa cells at $3 \times 10^{-5}$M. At pH 5.6, 71% of E. coli were killed by Chybrid at $3 \times 10^{-5}$M. This is equal to the concentration of #90-99 required to kill E. coli and two times higher than the concentration of C#90-99 required to kill E. coli (Table 4).

These results show that peptides containing amino acids 90-99 of B/PI retain bactericidal activity for P. aeruginosa and E. coli B, but at a much higher concentration than the 55 kD B/PI. Addition of an N-terminal cysteine residue to #90-99 peptide increased its activity about 10-fold.

Although P. cepacia and S. aureus were resistant to killing by the parent B/PI protein, they were susceptible to the #90-99 and C#90-99 peptides in the same concentration range as E. coli. Two other hydrophilic peptides with an N-terminal cysteine were not bactericidal at 100 times the effective concentration of C#90-99.

Other peptides shown in Table 2 were tested for biological activity at pH 5.6 against P. aeruginosa. The results are shown in Table 5. The peptides with asterisks are #90-99 and C#90-99 which serve as reference peptides to compare the biological activity of the other peptides.

TABLE 5

| Peptide Number | Code | Molar Concentration | Percent Killing |
|---|---|---|---|
| 1 | Signal | — | |
| *2 | 1 C#90-99 | $1.5 \times 10^{-6}$M | 83% |
| 3 | C#227-236 | — | |
| 4 | C#418-427 | — | |
| *5 | #90-99 | $1.5 \times 10^{-5}$M | 75% |
| 6a | 4 #27-37 | — | |
| 6b | C#27-37 | — | |
| 7a | #160-170 | — | |
| 7b | C#160-170 | — | |
| 8a | #86-99 | $6.0 \times 10^{-6}$M | 79% |
| *8b | C#86-99 | $1.5 \times 10^{-6}$M | 88% |
| | dimer 8b | $1.5 \times 10^{-6}$M | 52% |
| 9a | #90-102 | $6.0 \times 10^{-6}$M | 67% |
| *9b | C#90-102 | $1.5 \times 10^{-6}$M | 96% |
| 10a | 5 #118-127 | — | |
| 10b | C#118-127 | — | |
| 11 | F1 #1-26 | — | |
| 12 | F2 #38-62 | $1.5 \times 10^{-5}$M | 58% |
| 13 | F3 #63-99 | — | |
| 14 | F4 | - | |
| 15 | F5 | - | |
| 16 | F6 | — | |
| 17 | CHybrid | $3.0 \times 10^{-6}$M | 74% |
| 18 | Hybrid | $3.0 \times 10^{-5}$M | 79% |
| 19 | rand.90-99 | $1.2 \times 10^{-4}$M | 65% |
| 20a | C#90-99C | $3.0 \times 10^{-6}$M | 76% |
| | cyclic 20a | $3.0 \times 10^{-5}$M | 89% |
| 20b | #90-99C | $3.0 \times 10^{-6}$M | 75% |
| 21 | rand.90-99 | $1.5 \times 10^{-5}$M | 71% |
| 22 | #82-#108 | $6.0 \times 10^{-6}$M | 74% |
| 23 | C#82-108C | $3 \times 10^{-7}$M | 67% |
| 24 | Rustici#6 | $3.0 \times 10^{-5}$M | 72% |
| 24 | pure | — | |
| 25 | Rustici#2 | $6.0 \times 10^{-6}$M | 56% |
| | cyclic | $1.5 \times 10^{-5}$M | 73% |
| 26 | #91-92 wk→kw | $1.5 \times 10^{-5}$M | 61% |
| 27 | #93 w→f | $3.0 \times 10^{-5}$M | 49% |
| 28 | #93 w→a | $3.0 \times 10^{-5}$M | 68% |
| 29 | #100-109 | — | |
| 30 | #80-89 | — | |
| 31 | #83-92 | $3.0 \times 10^{-5}$M | 53% |
| 32 | #86-99 | $1.25 \times 10^{-4}$M | 33% |
| 33 | #94-103 | — | |
| 34 | #94-106 | — | |

TABLE 5-continued

| Peptide Number | Code | Molar Concentration | Percent Killing |
|---|---|---|---|
| 35 | #86-104 | $1.5 \times 10^{-7}$M | 58% |
| 36 | C#86-104C | $1.2 \times 10^{-4}$M | 39% |
| | cyclic | $1.5 \times 10^{-7}$M | 76% |

— = not active at concentrations of $1.2 \times 10^{-4}$M or less

The results show that peptides containing the amino acid residues #90-99 and an N-terminal cysteine residues are the most active peptides for bactericidal activity against P. aeruginosa. The most active peptides are #82-108, C82-108C, 86-104 and C86-104C (cyclic). These peptides have activity close to that of native B/PI. A dimerized peptide of amino acid residues 86-99 has less biological activity (52% killing) as the undimerized peptide #C86-99 (88%) at the same concentration but it acquired endotoxin neutralizing activity. The cyclic peptide containing C#90-99C has about 10-fold less bactericidal activity as the linear peptide with N- and C-terminal cysteines but it acquired endotoxin neutralizing activity (20a).

As discussed previously, the hybrid peptides had an activity for killing of bacteria between that of the C#90-99 peptide and the 90-99 peptide.

Peptides were also formed by randomizing the amino acid sequence of the 90-99 peptide. The results show that the peptide kkkwfrlakq (SEQ ID NO:36) (21) retained biological activity, but the activity of the sequence wkkfkgralk (SEQ ID NO:35) (19) was reduced 8-fold. Replacement of the tryptophan (w) in peptide 21 with alanine (a) (27) or phenylalanine (f) (28) had little or no effect on bacterial killing activity indicating that the residue at position 93 can be substituted with another hydrophobic or aliphatic amino acid without dramatically affecting activity.

Bactericidal Activity of Peptide-Protein Conjugates

The bactericidal activity of C#90-99 coupled to KLH (KLH-C#90-99) was also tested with P. aeruginosa, as shown in Table 6 and compared there with KLH conjugates of the inactive peptides, C#227-236 and C#418-427.

TABLE 6

Bactericidal Activity of B/PI Peptides
When Conjugated to a Protein Carrier

| Conjugate[a] | pH | % Killing of Psueodomonas aeruginosa | Peptide[b] Concentration |
|---|---|---|---|
| KLH-C#90-99 $9 \times 10^{-8}$M | 5.6 | 95 ± 3 | $1 \times 10^{-6}$M |
| | 7.0 | 90 ± 5 | 15:1[c] |
| KLH-C#227-236 $3 \times 10^{-7}$M | 5.6 | 0 | $5 \times 10^{-6}$M |
| | 7.0 | 0 | 16:1[c] |
| KLH-C#418-427 $5 \times 10^{-7}$M | 5.6 | 0 | $9 \times 10^{-6}$M |
| | 7.0 | 0 | 18:1[c] |

[a]$5 \times 10^6$ bacteria were incubated with a conjugate of peptide with Keyhole Limpet hemocyanin (KLH). The final concentration of conjugate is shown and was based on quantitation by amino acid composition.
[b]The final concentration of peptide is calculated from the amino acid composition of each conjugate compared with unsubstituted KLH.
[c]The ratio of peptide to carrier is shown and was also derived from the amino acid composition.

From the results for the amino acid composition of each purified conjugate and unconjugated carrier protein, the ratio of peptide to carrier and the final concentration of peptide were calculated, as shown in the right hand column of Table 5. Approximately 90-95% of $5 \times 10^6$ P. aeruginosa cells were killed by the KLH-C#90-99 conjugate at a peptide concentration calculated at $1\times10^{-6}$M. The bactericidal molar concentration of conjugate was very close to the $1.5\times10^{-6}$M of free C#90-99 peptide which caused 83% killing of this microorganism (Table 3, FIG. 1). Neither KLH-C#227-236 nor KLH-C#418-427 were bactericidal for *P. aeruginosa* at 5 and 9 times higher concentrations of peptide, respectively (Table 6). Similar results were obtained with the ovalbumin (OVA) conjugates of these three peptides (not shown). For example, at pH 5.6, 70% of *P. aeruginosa* cells were killed by OVA-C#90-99 conjugate at $4.5\times10^{-8}$M. This represents a peptide concentration of approximately $6\times10^{-6}$M and a molar ratio of C#90-99 peptide to OVA carrier of 9:1, both determined by calculation from the amino acid composition of the conjugate compared with unconjugated carrier.

The cysteine of the unconjugated C#90-99 peptide was 100% reduced. The bactericidal activity was not diminished when the C#90-99 peptide was coupled to KLH or OVA protein carriers, thus eliminating the reactive reduced sulfhydryl group. The free sulfhydryl group is lost through bond formation with the N-maleimidomethyl group of the activated carrier and this suggests that retention of antibacterial activity is not dependent on a disulfide bond, as might be in the #20-44 peptide of CAP37 and as it is in the defensin molecules.

EXAMPLE 3

Assay of Peptides for Neutralization of Endotoxin

Synthetically produced peptides were assayed for the ability to neutralize endotoxin in the LAL.

Limulus Amoebocyte Lysate Assay

The ability of synthetic peptides to neutralize endotoxin was detected with the E-TOXATE kit manufactured by Sigma Chemicals, St. Louis, Mo. The concentration of peptide required to completely inhibit the coagulation of LAL driven by *E. coli* 055: B5 LPS was determined by dose response and as outlined in technical bulletin #210 of Sigma Chemicals. Peptide was incubated with LPS at room temperature for 10 minutes in 100 µl of a 1:2 dilution of pyrogen-free saline, pH 6.4. The reaction was started by addition of 100 µl of amoebocyte lysate and the final volume was 200 µl. The results for some of the peptides are shown in Table 7.

TABLE 7

Synthetic Peptides With Endotoxin-Neutralizing Capacity

| Peptide Number | Code | Synthetic Peptide | Effective Dose M ($\times 10^{-4}$) | (µg/0.2 ml)* |
|---|---|---|---|---|
| 7a | #160-170 | kkiesalrnkm (SEQ ID NO:16) | 4.5 | 119 |
| 3 | C#227-236 | cefysenhhnp(g) (SEQ ID NO:17) | 1.2 | 34 |
| 4 | C#418-427 | cneklqkgfpl (SEQ ID NO:18) | 1.5 | 38 |
| 18 | Hybrid | efysenhhnpkwkaqkrflk (SEQ ID NO:11) | 3.0 | 155 |
| 17 | CHybrid | cefysenhhnpkwkaqkrflk (SEQ ID NO:12) | 1.2 | 81 |
| B/PI | | | 0.00015 | 0.165 |

*The dose of peptide required to inhibit clotting of LAL by 100%. Each tube contained 0.04 endotoxin units of *E. coli* LPS.

Figure 2:
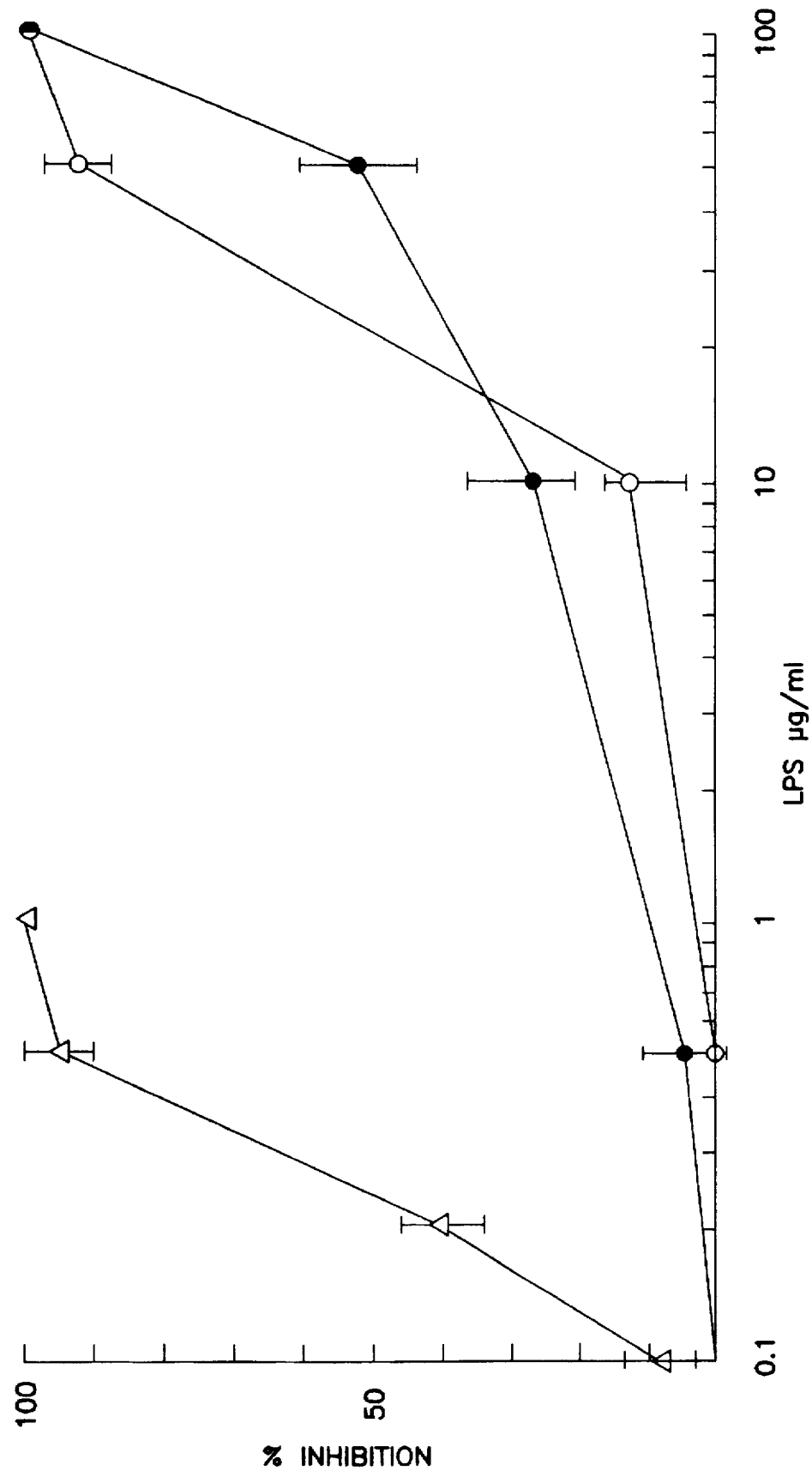
FIG. 2 shows the percent inhibition by purified LPS from *P. aeruginosa* 27312 (List Biological Laboratories, Campbell, Calif.) of the bactericidal activity of 2.3 µg/ml of C#90-99 (o—o;n=3) peptide or 23 µg/ml #90-99 (●—●) peptide or B/PI (Δ—Δ). Peptide was incubated at pH 5.6 with LPS for 15 minutes before the addition of 5×10$^6$ CFU of *P. aeruginosa* cells.

Although they were bactericidal for *E. coli*, linear peptides including amino acid sequence of #90-99 did not neutralize the procoagulant effects of *E. coli* endotoxin on LAL. The highest concentration of each peptide tested was $4.5\times10^{-4}$M. Linear peptides C#90-99, #90-99, C#89,90, #86-99, #86-104, and #90-102 did not neutralize endotoxin in the LAL. However as shown in FIG. 2, the C#90-99 and #90-99 peptides will bind to purified LPS from *P. aeruginosa* and that binding inhibits the bactericidal activity of the peptides. The $ID_{50}$ for C#90-99 was approximately 21 µg/ml and for #90-99 was approximately 42 µg/ml.

Three peptides with 11 amino acid residues were capable of neutralizing endotoxin in the Limulus assay. The concentration of peptide required for 100% inhibition of LPS-induced gelation of the amoebocyte lysate was determined by dose response. The endotoxin-neutralizing activity of the peptides was comparatively weak and is shown in Table 7. The most active endotoxin neutralizing peptide was C#227-236, which neutralized 0.04 endotoxin units of *E. coli* 055: B5 LPS when at a peptide concentration of $1.2\times10^{-4}$M. The C#418-427 peptide was closely similar and neutralized endotoxin at $1.5\times10^{-4}$M. The third peptide with neutralizing capacity (#160-170) was considerably less active than the aforementioned peptides and neutralized endotoxin at $4.5\times10^{-4}$M.

A hybrid peptide of the C#227-236 and #90-99 peptides (CHybrid, Table 2) was synthesized and tested for endotoxin neutralization (Table 7) and killing of *P. aeruginosa* and *E. coli* (Table 4). The CHybrid molecule completely neutralized endotoxin at the same concentration ($1.2\times10^{-4}$M) as did the original C#227-236 peptide. The Hybrid molecule without the N-terminal cysteine (Hybrid, Table 7) required two times more peptide for endotoxin neutralization than was required in the case of CHybrid. All results in Table 7 were reproduced without variation in at least two different experiments.

Other peptides were tested for endotoxin neutralizing activity as shown in Table 8. The asterisks identify reference peptides that have endotoxin neutralizing activity.

TABLE 8

| Peptide Number | Code | Effective Dose Endotoxin Neutralization (Molar Concentration) |
|---|---|---|
| 1 | Signal | — (SEQ ID NO:13) |
| 2 | 1 C#90-99 | — (SEQ ID NO:7) |
| *3 | C#227-236 | $1.2 \times 10^{-4}$M (SEQ ID NO:17) |
| *4 | C#418-427 | $1.5 \times 10^{-4}$M (SEQ ID NO:18) |
| 5 | #90-99 | — (SEQ ID NO:6) |
| 6a | 4 #27-37 | — (SEQ ID NO:14) |
| 6b | C#27-37 | — (SEQ ID NO:41) |
| *7a | #160-170 | $4.5 \times 10^{-4}$M (SEQ ID NO:16) |
| 7b | C#160-170 | $4.5 \times 10^{-4}$M (SEQ ID NO:42) |
| 8a | #86-99 | — (SEQ ID NO:9) |
| 8b | C#86-99 dimer 8b | — (SEQ ID NO:10) $3.0 \times 10^{-4}$M |
| 9a | #90-102 | — (SEQ ID NO:8) |
| 9b | C#90-102 | — (SEQ ID NO:27) |
| 10a | 5 #0118-127 | — (SEQ ID NO:15) |
| 10b | C#118-127 | — (SEQ ID NO:15) |
| 11 | F1 #1-26 | $7.5 \times 10^{-5}$M (SEQ ID NO:21) |
| 12 | F2 #38-62 | $7.5 \times 10^{-5}$M (SEQ ID NO:32) |
| 16 | F6 | $1.5 \times 10^{-4}$M (SEQ ID NO:47) |
| 17 | CHybrid | $1.2 \times 10^{-4}$M (SEQ ID NO:12) |
| 18 | Hybrid | $3.0 \times 10^{-4}$M (SEQ ID NO:11) |
| 19 | rand. 90-99 | — (SEQ ID NO:35) |
| 20a | #C90-99C cyclic 20A | — (SEQ ID NO:25) $4.5 \times 10^{-4}$M |
| 20b | #90-99C | — (SEQ ID NO:26) |
| 21 | rand. 90-99 | — (SEQ ID NO:36) |
| 22 | #82-108 | $3.0 \times 10^{-5}$M (SEQ ID NO:20) |
| 23 | #C#82-108C | $3.0 \times 10^{-5}$M (SEQ ID NO:28) |
| 24 | Rustici #6 | — (SEQ ID NO:48) |
| 24 | pure | $3.0 \times 10^{-4}$ (SEQ ID NO:48) |
| 25 | Rustici #2 | — (SEQ ID NO:49) |

TABLE 8-continued

| Peptide Number | Code | Effective Dose Endotoxin Neutralization (Molar Concentration) |
|---|---|---|
| | cyclic 25 | $4.5 \times 10^{-4}$M |
| 26 | rand #90-99 | $3.0 \times 10^{-4}$M (SEQ ID NO:24) |
| 27 | #93W-f | — (SEQ ID NO:38) |
| 28 | #93W-a | — (SEQ ID NO:39) |
| 29 | #100-109 | $2.2 \times 10^{-4}$M (SEQ ID NO:51) |
| 30 | #80-89 | $4.5 \times 10^{-4}$M (SEQ ID NO:52) |
| 31 | #83-92 | $2.2 \times 10^{-4}$M (SEQ ID NO:53) |
| 32 | #86-95 | $4.5 \times 10^{-4}$M (SEQ ID NO:54) |
| 33 | #95-104 | $4.5 \times 10^{-4}$M (SEQ ID NO:55) |
| 34 | #97-106 | $7.5 \times 10^{-4}$M (SEQ ID NO:56) |
| 35 | #86-104 | $4.5 \times 10^{-4}$M (SEQ ID NO:19) |
| 36 | C#86-104C | $7.5 \times 10^{-4}$M (SEQ ID NO:29) |
| | cyclic 36 | $2.25 \times 10^{-4}$M (SEQ ID NO:34) |

— = not active at concentrations of $4.5 \times 10^{-4}$M or less.

The results show that the reference peptides #160–170 (7a), C#227–236 (3), C#418–427 (4) demonstrated endotoxin neutralizing activity. Other active peptides include a peptide containing amino acids 1–26, the F6 peptide (16) and the pure Rustici peptide, peptide with amino acids 82–108 and a peptide with amino acids 86–104.

Linear peptides containing amino acids #90–99 did not have endotoxin neutralizing activity but a dimer of and cyclic compound of C#90–99C did acquire endotoxin neutralizing capability.

Several of the synthetic peptides have both bactericidal activity and endotoxin neutralizing activity, those peptides are as shown in Table 9.

TABLE 9

| Peptide Number | Code | Bactericidal Activity for pH 5.6 P. aeruginosa | Endotoxin Neutralization |
|---|---|---|---|
| 8b | dimer (C#86-99) | $1.5 \times 10^{6}$M | $3.0 \times 10^{4}$M |
| 12 | f2 #38-62 | $1.5 \times 10^{5}$M | $7.5 \times 10^{5}$M |
| 17 | CHybrid | $3.0 \times 10^{6}$M | $1.2 \times 10^{4}$M |
| 18 | Hybrid | $3.0 \times 10^{5}$M | $3.0 \times 10^{4}$M |
| 20a | Cyclic (C#90-99) | $1.5 \times 10^{6}$M | $4.5 \times 10^{4}$M |
| 22 | #82-108 | $6.0 \times 10^{8}$M | $2.0 \times 10^{5}$M |
| 23 | C#82-108C | $3.0 \times 10^{7}$M | $3.0 \times 10^{5}$M |
| 25 | cyclic 25 | $1.5 \times 10^{5}$M | $4.5 \times 10^{4}$M |
| 26 | kwkfkqralk | $1.0 \times 10^{5}$M | $3.0 \times 10^{4}$M |
| 35 | #86-104 | $1.5 \times 10^{7}$M | $4.5 \times 10^{4}$M |
| 36 | C#86-104C | $1.2 \times 10^{4}$M | $7.5 \times 10^{5}$M |
| | cyclic 36 | $1.5 \times 10^{7}$M | $2.25 \times 10^{4}$M |

The hybrid molecules are synthetic peptides including the amino acid sequences for #90–99 and #227–236. The hybrid peptides retained both bactericidal activity and endotoxin neutralizing activity comparable to either of those peptides alone. A dimer of C#86-99 and a cyclic peptide of C#90-99C retained bactericidal activity and acquired endotoxin neutralizing activity not present in the linear peptides (C#90–99C and C#86–99). A peptide including amino acids 90–99 can have both bactericidal and endotoxin neutralizing activity whether in linear or cyclic form such as peptides including amino acid sequences 82–108 and 86–104. Thus, bactericidal activity is associated with the peptides having amino acids 90–99 and endotoxin neutralizing activity can also be associated with a peptide having this sequence depending on its conformation.

EXAMPLE 4

Inhibition of Bactericidal Activity by Incubation with Endotoxin

Inhibition of bactericidal killing by LPS from *P. aeruginosa* ATCC 27312 (List Biological laboratories, Campbell, Calif.) was determined with LPS suspended in 0.1% triethylamine. LPS and peptide were incubated at pH 5.6 in 0.85 ml of buffer for 15 minutes at which time 0.15 ml of bacteria were added. Bactericidal effects were determined as described previously. Where an inhibitory dose $ID_{50}$ is indicated, it was determined by linear regression analysis after dose response experiments.

The results shown in FIG. 2 indicate that the #90–99 peptides will bind to purified LPS from *P. aeruginosa* and inhibit killing of *P. aeruginosa* by either of these peptides. The 50% inhibitory dose ($ID_{50}$) of LPS with C#90-99 was approximately 21 µg/ml, while the $ID_{50}$ of LPS with peptide #90-99 was approximately 45 µg/ml of LPS. Killing of *P. aeruginosa* was also inhibited by LPS from *E. coli* 0111:B4 (not shown), but inhibition of bacterial killing by both C#90–99 and #90–99 peptides required 40% more *E. coli* LPS (not shown) than was required with LPS from *P. aeruginosa* (FIG. 2).

These results indicate that the bactericidal function of B/PI can be located to a linear amino acid sequence including amino acid residues #90-99. An endotoxin neutralizing function can be assigned to the same location but appears conformation dependent.

EXAMPLE 5

Toxicity of Synthetic Peptides for Eukaryotic Cells

The synthetic peptides were assayed for toxicity to cultured eukaryotic cells. Human lung fibroblasts were grown in monolayers in Dulbecco's Modified Eagles' Medium (DMEM) with 10% fetal calf serum (FCS) and originated as primary cultures of lung mesenchymal cells. The cells were trypsinized, washed with either DMEM plus FCS or phosphate-buffered saline (PBS), pH 7.4, and incubated with peptide at a final cell concentration of $1 \times 10^7$/ml. Nine volumes of cell suspension were diluted with one volume of 0.4% trypan blue and the cells were counted with a hemocytometer, while also determining the fraction of cells which were increased in permeability to dye. There was no significant loss of cell number due to exposure of the fibroblasts to peptide.

The results are shown in Table 10.

TABLE 10

Effects of Synthetic Peptides on Viability of Human Lung Fibroblasts

| Peptide Number | Synthetic Peptide | Percent Viability[a] | |
|---|---|---|---|
| | | DMEM | PBS |
| Control | | 98.5 | 93.1 |
| #90-99 | kwkaqkrflk[b] (SEQ ID NO:6) | 98.0 | 89.4 |
| C#90-99 | ckwkaqkrflk[c] (SEQ ID NO:7) | 98.4 | 94.7 |
| Hybrid | efysenhhnpkwkaqkrflk[b] (SEQ ID NO:11) | 98.8 | 95.6 |
| CHybrid | cefysenhhnpkwkaqkrflk[c] (SEQ ID NO:12) | 99.2 | 92.3 |

[a] Viability was determined by trypan blue exclusion following incubation of cells with peptide for 30 minutes in DMEM plus 10% FCS or in PBS, pH 7.4.
[b] Final concentration of $1.5 \times 10^{-4}$M.
[c] Final concentration of $1.5 \times 10^{-5}$M.

The toxicity of four of the bactericidal peptides for mammalian cells was tested by incubation of human lung fibroblasts with 10 times the bactericidal peptide concentration effective with *P. aeruginosa*. There was no significant increase in permeability to trypan blue (Table 10) as a result of exposure to any of the peptides tested.

EXAMPLE 6

Formation of Monoclonal and Polyclonal Antibodies to Peptides

Peptides were conjugated to KLH or ovalbumin carrier proteins as described in Example 1. The following peptide-carrier conjugates were made:

90-99
227-236
418-427
27-37
118-127
160-169

These peptide carrier molecules were injected into rabbits using standard methods. Antibodies to B/PI were obtained in a similar manner or can be obtained from Chemicon Int'l, Inc. (Femecula, Calif.). Both monoclonal and polyclonal antibodies were obtained using standard methods as described in *Antibodies: A Laboratory Manual*, Harlow and Lane, Cold Spring Harbor Laboratory (1988).

Polyclonal antisera and monoclonal antibodies specific for peptides were analyzed by Western blot. The results are shown in FIG. 3.

Figure 3:
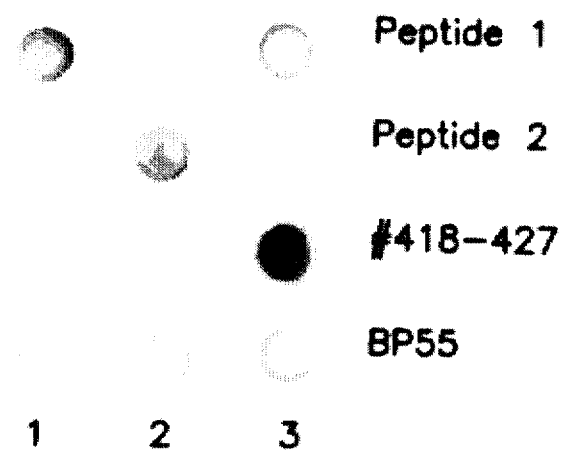
FIG. 3 shows Western dot blot of peptides derived from BP55 using rabbit polyclonal sera. Lane 1 peptide #90-99, Line 2 peptide #227-236, Lane 3 peptide #418-427. Each lane also contained BP55. The lanes were probed with antisera from rabbits immunized with #90-99, #227-236, #418-427, respectively.

Dot blots of peptide-OVA conjugates on nitrocellulose strips are shown in FIG. 3 and were stained by Western blot method. Strips were blocked with 1.5% gelatin and incubated at room temperature with a 1:2000 dilution of rabbit anti-peptide antibody followed by a 1:1000 dilution of goat anti-rabbit IgG coupled to alkaline phosphatase. Color was developed by incubation with substrate for the enzyme as described by the manufacturer. Rabbit antibody to peptide 1 (#90-99; lane 1), reacted only with peptide 1 and weakly with B/PI. Antibody to peptide 2 (#227-236, lane 2) reacted strongly with peptide 2 and B/PI and cross-reacted weakly with other peptides. Antibody to peptide #418-427 (lane 3) reacted strongly with the homologous peptide but weakly with B/PI. Monoclonal antibody designated ANH13 specific for B/PI (Wasiluk et al., cited supra.) also reacted strongly with peptide 2 (not shown). The antibody to peptides #227-236 and #418-427 will be cross-absorbed with heterologous peptide-OVA conjugates to improve specificity.

EXAMPLE 7

Preparation of cDNA clone encoding B/PI (1–496)

A cDNA encoding a portion of B/PI has been isolated. The cDNA clone has been subcloned into a baculovirus vector for expression in insect cell culture. The cDNA clone was obtained by standard methods as described by Maniates et al., *A Guide to Molecular Cloning* (1989). A full length cDNA library coding for B/PI was obtained from a cDNA library obtained from ClonTech Laboratories, Inc., Palo Alto, Calif. The cDNA library was screened using monoclonal antibodies for B/PI and positive plaques were amplified and sequenced using standard methods. The sequence of the full length cDNA is shown in FIG. 8.

The cDNA for B/PI was subcloned in the transfer vector pVC1393 or the Bluebac His III vector (Invitrogen Corp., San Diego, Calif.) using restriction enzymes. The cDNA was inserted into the correct orientation at EcoRI site for pV139 or a BamHI site for Bluebac His III vector. Coinfection of insect cells with the recombinant transfer vector and the wild type baculovirus led to the isolation of a recombinant B/PI as detected by Western blot using monoclonal antibodies to B/PI.

Primers were selected to amplify portions of the cDNA sequence for B/PI and are shown in FIG. 4 in the boxed regions and with letter designations. Primers were selected to amplify fragments encoding amino acids 1–110. Primer pairs shown in FIG. 4 that can be utilized to amplify cDNA coding for amino acids 1–110 include primer GI and C. The primers are designed to be complementary to the coding sequence at these regions of the cDNA sequence and preferably are about 1–30 nucleotides long. Primer sequences can be selected based on well established principles known to those of skill in the art and can include noncomplementary sequences such as restriction enzyme recognition sequences and sequences coding for amino acids such as cysteine or methionine. For example the 5' to 3' primers have a BamHI restriction site and the 3' to 5' primers have a BglII restriction site and a stop codon.

Figure 5:
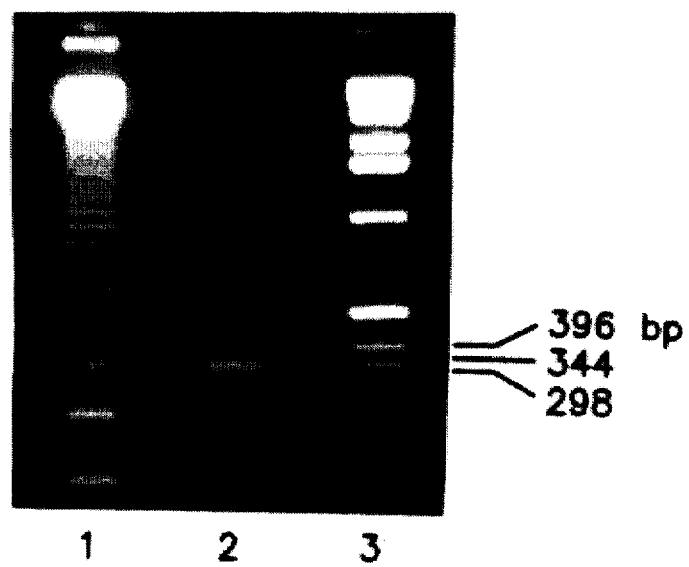
FIG. 5 represents agarose gel electrophoresis of a PCR product generated with primers GI and C as shown in FIG. 4. Lane 1 is a 0.1 Kb standard ladder; Lane 2 is the PCR product; and Lane 3 is a standard 1 Kb ladder. Bands were visualized with ethidium bromide.

A fragment of the cDNA sequence encoding amino acids 1–110 was amplified using primers GI and C. The reverse primer C is the inverse complement of the sequence shown under primer C followed by a stop codon and an extended BglII restriction site. The PCR product of this primer was estimated to be 353 base pairs and was isolated by agarose gel electrophoresis. See FIG. 5 (Lane 2). This fragment codes for amino acids 1–110 of the mature B/PI protein.

The PCR reaction was carried out by incubation of primers (as shown in FIG. 4) and the cDNA insert for B/PI with PCR buffer, dNTPs and Taq polymerase as described in Larrick et al., *Bio/Tech*, 7:934 (1989). Each PCR contains 100pg-10ng of template oligonucleotide, 10–40 nmole each of appropriate combination of primers, 20 mM Tris-HCl, pH 8.3 at 20° C., 1.5 mM $MgCl_2$, 25 mM KCl, 50 µM of each dNTP and 2.5 units of Taq polymerase. The PCRs were carried out for 25–40 cycles on thermal cycler using the following conditions:94° C., 1 minute; 42–55° C., 2 minutes; 72° C., 3 minutes. PCR fragments were purified by agarose gel electrophoresis, digested with restriction enzymes and ligated into the baculovirus transfer vector. Sequencing of the PCR product insert in the transfer vector was by the dideoxynucleotide chain termination method with Sequenase (U.S. Biochemicals) and by direct sequencing of the double-stranded DNA of baculovirus. Wang et al., *J. Virol Meth.*, 31:113 (1991).

Plasmid pVL1393 is a vector that contains the polyhedron gene and all known translational regulatory sequences upstream and downstream of the ATG start site of the polyhedron gene. The natural ATG has been removed through site directed mutagenesis so that translation begins with the ATG of the foreign cDNA inserted at any of a number of cloning sites within the polyhedron gene of the transfer vector. The Bluebac His III vector is a vector that contains a B-galactosidase gene under control of the polyhedron gene promoter. When a recombinant fragment is inserted into a BamHI site it forms a DNA sequence coding for a B-gal fusion protein. A restriction map is shown in FIG. 7. The transfer vector wild type baculovirus, AcMNPv and *Spodoptera frugiperda* Sf9 host cells have been purchased from Invitrogen Corp., San Diego, Calif. A full-length cDNA for B/PI has been subcloned by ligation into the EcoRI site of the pVL1393 baculovirus transfer vector. A subclone of the correct orientation was established by restriction mapping.

Expression of B/PI In Insect Cells Infected with a Recombinant Baculovirus.

Baculoviruses have been developed for high-level expression of foreign genes in insect cells. Luckow et al, *Biotech*, 6:47 (1988). Glycosylations are more fully accomplished in this system than in other expression systems and the abundant expression of many mammalian proteins which are appropriately folded, processed and functionally active has been achieved. In this system, the cDNA of the foreign gene is ligated into a plasmid transfer vector such as pVL1393 containing a strong promoter of the baculovirus polyhedron gene. Under the control of this promoter, the inserted cDNA should be overexpressed after recombination of the polyhedron gene (with its insert) and the infectious wild-type baculovirus (AcMNPV). This occurs during coinfection of permissive *Spodoptera frugiperda* (Sf9) cells with AcMNPV and the transfer vector.

Recombinant virus form a visibly different plaque morphology which provides a convenient means of selecting for recombinant virus. In addition, inserts in the Bluebac His III vector can be detected by expression of B-gal fusion proteins. Insect cell culture plaques expressing the fusion protein turn blue when supplied with a labelled substrate. Alternatively, plaques can be detected by an antibody method. Plaques with highest level expression of the foreign gene can be identified immunologically and the purified recombinant virus used for large scale production of foreign protein after infection of Sf9 insect cells.

Cells and Transfections.

Recombination of transfer vector with wild-type baculovirus AcMNPV can be performed by cotransfection of Sf9 cells. The Sf9 cells are maintained as 'monolayer' cultures at 28° C. in Grace's medium (Invitrogen) supplemented with 10% heat-inactivated fetal calf serum and 50 µg/ml gentamycin. For large scale virus preparations and production of recombinant protein, cells can be grown in suspension in the same medium. Transfections and plaque assays can be performed essentially as described by Summers et al., *A Manual for Baculovirus Express System, Tex. Agric. Exp. Stn:Bull*, 1555 (1987), but with some modification. Viral plaques with an altered plaque morphology can not only be picked, but infected cells can also be assayed for the presence of B/PI and with rabbit antibodies to synthetic peptides based on the structure of B/PI.

Screening for expression by recombinants can be as described by Capone, *J. Gen. Anal Techn.*, 6:62 (1989). The agar overlay can be carefully removed from plates containing plaques and placed plaque side up in a sterile culture dish. A disk of nitro-cellulose filter can be placed on the agar for 5 minutes, peeled off and placed in blocking solution (10% calf serum in TBST). A 30-minute blocking step can be followed by incubation with antibody to B/PI, then with a second antibody to mouse immunoglobulin which is coupled with alkaline phosphatase. Finally, the disk can be stained with substrate for the enzyme, and plaques with strong expression are identified. Selected recombinant virus can be plaque-purified four times and the purified virus can be expanded and used in large scale infections of Sf9 cells.

Sf9 cells have been maintained and transferred in culture without difficulty for the past two years. Wild-type and recombinant plaques have been recognized using a Bluebac His III transfer vector with cDNA insert and gene for beta-galactosidase. About 200 plaques/plates were detected that expressed the full length B/PI (data not shown).

Preparation of Cell Extracts.

Foreign proteins are rarely secreted by Sf9 cells infected with recombinant baculovirus and recombinant proteins are usually isolated from lysates of infected cells. Culture supernatants are checked for secretion of truncated B/PI, but in the event it is not there B/PI fragments are isolated from cell lysates. Infected cells are harvested and washed twice in ice-cold PBS, pH 6.2. Subsequent manipulations are carried out at 4° C. Cells are collected by centrifugation at 500xg for 10 minutes, then resuspended in lysis buffer (20 mM HEPES, pH 7.5, 5mM KCl, 0.5 mM DTT, 1 mM PMSF) and maintained on ice for 10 minutes. Cells are then disrupted by homogenization. Nuclei are removed by sedimentation and the supernatant clarified by centrifugation at 26,000xg for 20 minutes. Samples of culture supernatant and cell lysate supernatant are subjected to SDS PAGE, electrotransfer of proteins and Western blot analysis.

Purification of Truncated Recombinant Fragments of B/PI.

Recombinant products can be purified from infected cells by immunoaffinity chromatography with the appropriate immobilized rabbit anti-peptide antibody or a mouse monoclonal antibody to B/PI. B/PI was reproducibly purified by application of partially purified samples of 2 mg protein to a 1.5×180 cm Toyopearl HW55S (Toso Haas) column or 200 mg protein to a TSX2000 HPLC (Beckman) column. The elution buffer for both columns is 0.05M glycine buffer, pH 2.5, with 0.5M NaCl. Recovery of B/PI protein was excellent and 100% of bactericidal activity is retained. The bactericidal activity of B/PI in this buffer was stable at 4° C. and at −70° C. for prolonged periods. The columns resolve protein standards over the range of 2–70 kD and can be used for all steps separation of fragments of B/PI by molecular weight. Reverse phase HPLC can be used if necessary.

All publications and patent applications in this specification are indicative of the level of ordinary skill in the art to which this invention pertains. All publications and patent applications are herein incorporated by reference to the same extent as if each individual publication or patent application was specifically and individually indicated by reference.

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

---

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 900 base pairs
        ( B ) TYPE: nucleic acid
        ( C ) STRANDEDNESS: single -continued ( D ) TOPOLOGY: linear ( i i ) MOLECULE TYPE: DNA (genomic)

( v i ) ORIGINAL SOURCE:
    ( A ) ORGANISM: Nucleotide coding for B/PI ( i x ) FEATURE:
    ( A ) NAME/KEY: CDS
    ( B ) LOCATION: 1..900

( x i ) SEQUENCE DESCRIPTION: SEQ ID NO:1:

```
ATG

```
CCA  GTG  ATG  GAG  TTT  CCC  GCT  GCC  CAT  GAC  CGC  ATG  GTA  TAC  CTG  GGC                864
Pro  Val  Met  Glu  Phe  Pro  Ala  Ala  His  Asp  Arg  Met  Val  Tyr  Leu  Gly
          275                      280                      285

CTC  TCA  GAC  TAC  TTC  TTC  AAC  ACA  GCC  GGG  CTT  GTA                                     900
Leu  Ser  Asp  Tyr  Phe  Phe  Asn  Thr  Ala  Gly  Leu  Val
          290                      295                      300
```

( 2 ) INFORMATION FOR SEQ ID NO:2:

( i ) SEQUENCE CHARACTERISTICS:
      ( A ) LENGTH: 300 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met  Arg  Glu  Asn  Met  Ala  Arg  Gly  Pro  Cys  Asn  Ala  Pro  Arg  Trp  Val
 1                    5                        10                       15

Ser  Leu  Met  Val  Leu  Val  Ala  Ile  Gly  Thr  Ala  Val  Thr  Ala  Ala  Val
               20                        25                       30

Asn  Pro  Gly  Val  Val  Val  Arg  Ile  Ser  Gln  Lys  Gly  Leu  Asp  Tyr  Ala
          35                             40                       45

Ser  Gln  Gln  Gly  Thr  Ala  Ala  Leu  Gln  Lys  Glu  Leu  Lys  Arg  Ile  Lys
     50                        55                       60

Ile  Pro  Asp  Tyr  Ser  Asp  Ser  Phe  Lys  Ile  Lys  His  Leu  Gly  Lys  Gly
 65                    70                        75                       80

His  Tyr  Ser  Phe  Tyr  Ser  Met  Asp  Ile  Arg  Glu  Phe  Gln  Leu  Pro  Ser
                    85                        90                       95

Ser  Gln  Ile  Ser  Met  Val  Pro  Asn  Val  Gly  Leu  Lys  Phe  Ser  Ile  Ser
               100                       105                      110

Asn  Ala  Asn  Ile  Lys  Ile  Ser  Gly  Lys  Trp  Lys  Ala  Gln  Lys  Arg  Phe
          115                            120                      125

Leu  Lys  Met  Ser  Gly  Asn  Phe  Asp  Leu  Ser  Ile  Glu  Gly  Met  Ser  Ile
     130                       135                      140

Ser  Ala  Asp  Leu  Lys  Leu  Gly  Ser  Asn  Pro  Thr  Ser  Gly  Lys  Pro  Thr
145                      150                       155                      160

Ile  Thr  Cys  Ser  Ser  Cys  Ser  Ser  His  Ile  Asn  Ser  Val  His  Val  His
               165                       170                      175

Ile  Ser  Lys  Ser  Lys  Val  Gly  Trp  Leu  Ile  Gln  Leu  Phe  His  Lys  Lys
               180                       185                      190

Ile  Glu  Ser  Ala  Leu  Arg  Asn  Lys  Met  Asn  Ser  Gln  Val  Cys  Glu  Lys
          195                            200                      205

Val  Thr  Asn  Ser  Val  Ser  Ser  Lys  Leu  Gln  Pro  Tyr  Phe  Gln  Thr  Leu
     210                       215                      220

Pro  Val  Met  Thr  Lys  Ile  Asp  Ser  Val  Ala  Gly  Ile  Asn  Tyr  Gly  Leu
225                      230                       235                      240

Val  Ala  Pro  Pro  Ala  Thr  Thr  Ala  Glu  Thr  Leu  Asp  Val  Gln  Met  Lys
                    245                       250                      255

Gly  Glu  Phe  Tyr  Ser  Glu  Asn  His  His  Asn  Pro  Pro  Phe  Ala  Pro
                    260                       265                      270

Pro  Val  Met  Glu  Phe  Pro  Ala  Ala  His  Asp  Arg  Met  Val  Tyr  Leu  Gly
          275                            280                      285

Leu  Ser  Asp  Tyr  Phe  Phe  Asn  Thr  Ala  Gly  Leu  Val
     290                       295                      300
```

( 2 ) INFORMATION FOR SEQ ID NO:3:

( i ) SEQUENCE CHARACTERISTICS:
    ( A ) LENGTH: 1653 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Coding for C/PI protein ( i x ) FEATURE:
    ( A ) NAME/KEY: CDS
    ( B ) LOCATION: 1..1464

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | AGA | GAG | AAC | ATG | GCC | AGG | GGC | CCT | TGC | AAC | GCG | CCG | AGA | TGG | GTG | 48 |
| Met | Arg | Glu | Asn | Met | Ala | Arg | Gly | Pro | Cys | Asn | Ala | Pro | Arg | Trp | Val | |
| 1 | | | | 5 | | | | | 10 | | | | | 15 | | |
| TCC | CTG | ATG | GTG | CTC | GTC | GCC | ATA | GGC | ACC | GCC | GTG | ACA | GCG | GCC | GTC | 96 |
| Ser | Leu | Met | Val | Leu | Val | Ala | Ile | Gly | Thr | Ala | Val | Thr | Ala | Ala | Val | |
| | | | 20 | | | | | 25 | | | | | 30 | | | |
| AAC | CCT | GGC | GTC | GTG | GTC | AGG | ATC | TCC | CAG | AAG | GGC | CTG | GAC | TAC | GCC | 144 |
| Asn | Pro | Gly | Val | Val | Val | Arg | Ile | Ser | Gln | Lys | Gly | Leu | Asp | Tyr | Ala | |
| | | 35 | | | | | 40 | | | | | 45 | | | | |
| AGC | CAG | CAG | GGG | ACG | GCC | GCT | CTG | CAG | AAG | GAG | CTG | AAG | AGG | ATC | AAG | 192 |
| Ser | Gln | Gln | Gly | Thr | Ala | Ala | Leu | Gln | Lys | Glu | Leu | Lys | Arg | Ile | Lys | |
| | 50 | | | | | 55 | | | | | 60 | | | | | |
| ATT | CCT | GAC | TAC | TCA | GAC | AGC | TTT | AAG | ATC | AAG | CAT | CTT | GGG | AAG | GGG | 240 |
| Ile | Pro | Asp | Tyr | Ser | Asp | Ser | Phe | Lys | Ile | Lys | His | Leu | Gly | Lys | Gly | |
| 65 | | | | 70 | | | | | 75 | | | | | 80 | | |
| CAT | TAT | AGC | TTC | TAC | AGC | ATG | GAC | ATC | CGT | GAA | TTC | CAG | CTT | CCC | AGT | 288 |
| His | Tyr | Ser | Phe | Tyr | Ser | Met | Asp | Ile | Arg | Glu | Phe | Gln | Leu | Pro | Ser | |
| | | | | 85 | | | | | 90 | | | | | 95 | | |
| TCC | CAG | ATA | AGC | ATG | GTG | CCC | AAT | GTG | GGC | CTT | AAG | TTC | TCC | ATC | AGC | 336 |
| Ser | Gln | Ile | Ser | Met | Val | Pro | Asn | Val | Gly | Leu | Lys | Phe | Ser | Ile | Ser | |
| | | | 100 | | | | | 105 | | | | | 110 | | | |
| AAC | GCC | AAT | ATC | AAG | ATC | AGC | GGG | AAA | TGG | AAG | GCA | CAA | AAG | AGA | TTC | 384 |
| Asn | Ala | Asn | Ile | Lys | Ile | Ser | Gly | Lys | Trp | Lys | Ala | Gln | Lys | Arg | Phe | |
| | | 115 | | | | | 120 | | | | | 125 | | | | |
| TTA | AAA | ATG | AGC | GGC | AAT | TTT | GAC | CTG | AGC | ATA | GAA | GGC | ATG | TCC | ATT | 432 |
| Leu | Lys | Met | Ser | Gly | Asn | Phe | Asp | Leu | Ser | Ile | Glu | Gly | Met | Ser | Ile | |
| | 130 | | | | | 135 | | | | | 140 | | | | | |
| TCG | GCT | GAT | CTG | AAG | CTG | GGC | AGT | AAC | CCC | ACG | TCA | GGC | AAG | CCC | ACC | 480 |
| Ser | Ala | Asp | Leu | Lys | Leu | Gly | Ser | Asn | Pro | Thr | Ser | Gly | Lys | Pro | Thr | |
| 145 | | | | 150 | | | | | 155 | | | | | 160 | | |
| ATC | ACC | TGC | TCC | AGC | TGC | AGC | AGC | CAC | ATC | AAC | AGT | GTC | CAC | GTG | CAC | 528 |
| Ile | Thr | Cys | Ser | Ser | Cys | Ser | Ser | His | Ile | Asn | Ser | Val | His | Val | His | |
| | | | | 165 | | | | | 170 | | | | | 175 | | |
| ATC | TCA | AAG | AGC | AAA | GTC | GGG | TGG | CTG | ATC | CAA | CTC | TTC | CAC | AAA | AAA | 576 |
| Ile | Ser | Lys | Ser | Lys | Val | Gly | Trp | Leu | Ile | Gln | Leu | Phe | His | Lys | Lys | |
| | | | 180 | | | | | 185 | | | | | 190 | | | |
| ATT | GAG | TCT | GCG | CTT | CGA | AAC | AAG | ATG | AAC | AGC | CAG | GTC | TGC | GAG | AAA | 624 |
| Ile | Glu | Ser | Ala | Leu | Arg | Asn | Lys | Met | Asn | Ser | Gln | Val | Cys | Glu | Lys | |
| | | 195 | | | | | 200 | | | | | 205 | | | | |
| GTG | ACC | AAT | TCT | GTA | TCC | TCC | AAG | CTG | CAA | CCT | TAT | TTC | CAG | ACT | CTG | 672 |
| Val | Thr | Asn | Ser | Val | Ser | Ser | Lys | Leu | Gln | Pro | Tyr | Phe | Gln | Thr | Leu | |
| | 210 | | | | | 215 | | | | | 220 | | | | | |
| CCA | GTA | ATG | ACC | AAA | ATA | GAT | TCT | GTG | GCT | GGA | ATC | AAC | TAT | GGT | CTG | 720 |
| Pro | Val | Met | Thr | Lys | Ile | Asp | Ser | Val | Ala | Gly | Ile | Asn | Tyr | Gly | Leu | |
| 225 | | | | 230 | | | | | 235 | | | | | 240 | | |
| GTG | GCA | CCT | CCA | GCA | ACC | ACG | GCT | GAG | ACC | CTG | GAT | GTA | CAG | ATG | AAG | 768 |
| Val | Ala | Pro | Pro | Ala | Thr | Thr | Ala | Glu | Thr | Leu | Asp | Val | Gln | Met | Lys | |

| | | | | | | | | | | | | | | | | |
|---|---|---|---|---|---|---|---|---|---|---|---|---|---|---|---|---|
| | | | 245 | | | | | 250 | | | | | 255 | | | |
| GGG | GAG | TTT | TAC | AGT | GAG | AAC | CAC | CAC | AAT | CCA | CCT | CCC | TTT | GCT | CCA | 816 |
| Gly | Glu | Phe | Tyr | Ser | Glu | Asn | His | His | Asn | Pro | Pro | Pro | Phe | Ala | Pro | |
| | | | 260 | | | | | 265 | | | | | 270 | | | |
| CCA | GTG | ATG | GAG | TTT | CCC | GCT | GCC | CAT | GAC | CGC | ATG | GTA | TAC | CTG | GGC | 864 |
| Pro | Val | Met | Glu | Phe | Pro | Ala | Ala | His | Asp | Arg | Met | Val | Tyr | Leu | Gly | |
| | | | 275 | | | | | 280 | | | | | 285 | | | |
| CTC | TCA | GAC | TAC | TTC | TTC | AAC | ACA | GCC | GGG | CTT | GTA | TAC | CAA | GAG | GCT | 912 |
| Leu | Ser | Asp | Tyr | Phe | Phe | Asn | Thr | Ala | Gly | Leu | Val | Tyr | Gln | Glu | Ala | |
| | | | 290 | | | | | 295 | | | | | 300 | | | |
| GGG | GTC | TTG | AAG | ATG | ACC | CTT | AGA | GAT | GAC | ATG | ATT | CCA | AAG | GAG | TCC | 960 |
| Gly | Val | Leu | Lys | Met | Thr | Leu | Arg | Asp | Asp | Met | Ile | Pro | Lys | Glu | Ser | |
| 305 | | | | 310 | | | | | 315 | | | | | 320 | | |
| AAA | TTT | CGA | CTG | ACA | ACC | AAG | TTC | TTT | GGA | ACC | TTC | CTA | CCT | GAG | GTG | 1008 |
| Lys | Phe | Arg | Leu | Thr | Thr | Lys | Phe | Phe | Gly | Thr | Phe | Leu | Pro | Glu | Val | |
| | | | | 325 | | | | | 330 | | | | | 335 | | |
| GCC | AAG | AAG | TTT | CCC | AAC | ATG | AAG | ATA | CAG | ATC | CAT | GTC | TCA | GCC | TCC | 1056 |
| Ala | Lys | Lys | Phe | Pro | Asn | Met | Lys | Ile | Gln | Ile | His | Val | Ser | Ala | Ser | |
| | | | 340 | | | | | 345 | | | | | 350 | | | |
| ACC | CCG | CCA | CAC | CTG | TCT | GTG | CAG | CCC | ACC | GGC | CTT | ACC | TTC | TAC | CCT | 1104 |
| Thr | Pro | Pro | His | Leu | Ser | Val | Gln | Pro | Thr | Gly | Leu | Thr | Phe | Tyr | Pro | |
| | | 355 | | | | | 360 | | | | | 365 | | | | |
| GCC | GTG | GAT | GTC | CAG | GCC | TTT | GCC | GTC | CTC | CCC | AAC | TCC | TCC | CTG | GCT | 1152 |
| Ala | Val | Asp | Val | Gln | Ala | Phe | Ala | Val | Leu | Pro | Asn | Ser | Ser | Leu | Ala | |
| | 370 | | | | | 375 | | | | | 380 | | | | | |
| TCC | CTC | TTC | CTG | ATT | GGC | ATG | CAC | ACA | ACT | GGT | TCC | ATG | GAG | GTC | AGC | 1200 |
| Ser | Leu | Phe | Leu | Ile | Gly | Met | His | Thr | Thr | Gly | Ser | Met | Glu | Val | Ser | |
| 385 | | | | | 390 | | | | | 395 | | | | | 400 | |
| GCC | GAG | TCC | AAC | AGG | CTT | GTT | GGA | GAG | CTC | AGG | CTG | GAT | AGG | CTG | CTC | 1248 |
| Ala | Glu | Ser | Asn | Arg | Leu | Val | Gly | Glu | Leu | Arg | Leu | Asp | Arg | Leu | Leu | |
| | | | | 405 | | | | | 410 | | | | | 415 | | |
| CTG | CAA | CTG | AAG | CAC | TCA | AAT | ATT | GGC | CCC | TTC | CCG | GTT | GAA | TTG | CTG | 1296 |
| Leu | Gln | Leu | Lys | His | Ser | Asn | Ile | Gly | Pro | Phe | Pro | Val | Glu | Leu | Leu | |
| | | | 420 | | | | | 425 | | | | | 430 | | | |
| CAG | GAT | ATC | ATG | AAC | TAC | ATT | GTA | CCC | ATT | CTT | GTG | CTG | CCC | AGG | GTT | 1344 |
| Gln | Asp | Ile | Met | Asn | Tyr | Ile | Val | Pro | Ile | Leu | Val | Leu | Pro | Arg | Val | |
| | | 435 | | | | | 440 | | | | | 445 | | | | |
| AAC | GAG | AAA | CTA | CAG | AAA | GGC | TTC | CCT | CTC | CCG | ACG | CCG | GCC | AGA | GTC | 1392 |
| Asn | Glu | Lys | Leu | Gln | Lys | Gly | Phe | Pro | Leu | Pro | Thr | Pro | Ala | Arg | Val | |
| | 450 | | | | | 455 | | | | | 460 | | | | | |
| CAG | CTC | TAC | AAC | GTA | GTG | CTT | CAG | CCT | CAC | CAG | AAC | TTC | CTG | CTG | TTC | 1440 |
| Gln | Leu | Tyr | Asn | Val | Val | Leu | Gln | Pro | His | Gln | Asn | Phe | Leu | Leu | Phe | |
| 465 | | | | | 470 | | | | | 475 | | | | | 480 | |
| GGT | GCA | GAC | GTT | GTC | TAT | AAA | TGAAGGCACC | AGGGGTGCCG | GGGGCTGTCA | | | | | | | 1491 |
| Gly | Ala | Asp | Val | Val | Tyr | Lys | | | | | | | | | | |
| | | | 485 | | | | | | | | | | | | | |

| | | | | | |
|---|---|---|---|---|---|
| GCCGCACCTG | TTCCTGATGG | GCTGTGGGGC | ACCGGCTGCC | TTTCCCCAGG | GAATCCTCTC | 1551 |
| CAGATCTTAA | CCAAGAGCCC | CTTGCAAACT | TCTTCGACTC | AGATTCAGAA | ATGATCTAAA | 1611 |
| CACGAGGAAA | CATTATTCAT | TGGAAAAGTG | CATGGTGTGT | AT | | 1653 |

( 2 ) INFORMATION FOR SEQ ID NO:4:

( i ) SEQUENCE CHARACTERISTICS:
    ( A ) LENGTH: 487 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

-continued

| | | | | | | | | | | | | | | |
|---|---|---|---|---|---|---|---|---|---|---|---|---|---|---|
| Met 1 | Arg | Glu | Asn | Met 5 | Ala | Arg | Gly | Pro | Cys 10 | Asn | Ala | Pro | Arg | Trp 15 | Val |
| Ser | Leu | Met | Val 20 | Leu | Val | Ala | Ile | Gly 25 | Thr | Ala | Val | Thr | Ala 30 | Ala | Val |
| Asn | Pro | Gly 35 | Val | Val | Val | Arg | Ile 40 | Ser | Gln | Lys | Gly | Leu 45 | Asp | Tyr | Ala |
| Ser | Gln 50 | Gln | Gly | Thr | Ala | Ala 55 | Leu | Gln | Lys | Glu | Leu 60 | Lys | Arg | Ile | Lys |
| Ile 65 | Pro | Asp | Tyr | Ser | Asp 70 | Ser | Phe | Lys | Ile | Lys 75 | His | Leu | Gly | Lys | Gly 80 |
| His | Tyr | Ser | Phe | Tyr 85 | Ser | Met | Asp | Ile | Arg 90 | Glu | Phe | Gln | Leu | Pro 95 | Ser |
| Ser | Gln | Ile | Ser | Met 100 | Val | Pro | Asn | Val | Gly 105 | Leu | Lys | Phe | Ser 110 | Ile | Ser |
| Asn | Ala | Asn 115 | Ile | Lys | Ile | Ser | Gly 120 | Lys | Trp | Lys | Ala | Gln 125 | Lys | Arg | Phe |
| Leu | Lys 130 | Met | Ser | Gly | Asn | Phe 135 | Asp | Leu | Ser | Ile | Glu 140 | Gly | Met | Ser | Ile |
| Ser 145 | Ala | Asp | Leu | Lys | Leu 150 | Gly | Ser | Asn | Pro | Thr 155 | Ser | Gly | Lys | Pro | Thr 160 |
| Ile | Thr | Cys | Ser | Ser 165 | Cys | Ser | Ser | His | Ile 170 | Asn | Ser | Val | His 175 | Val | His |
| Ile | Ser | Lys | Ser 180 | Lys | Val | Gly | Trp | Leu 185 | Ile | Gln | Leu | Phe | His 190 | Lys | Lys |
| Ile | Glu | Ser 195 | Ala | Leu | Arg | Asn | Lys 200 | Met | Asn | Ser | Gln | Val 205 | Cys | Glu | Lys |
| Val | Thr 210 | Asn | Ser | Val | Ser | Ser 215 | Lys | Leu | Gln | Pro | Tyr 220 | Phe | Gln | Thr | Leu |
| Pro 225 | Val | Met | Thr | Lys | Ile 230 | Asp | Ser | Val | Ala | Gly 235 | Ile | Asn | Tyr | Gly | Leu 240 |
| Val | Ala | Pro | Pro | Ala 245 | Thr | Thr | Ala | Glu | Thr 250 | Leu | Asp | Val | Gln | Met 255 | Lys |
| Gly | Glu | Phe | Tyr 260 | Ser | Glu | Asn | His | His 265 | Asn | Pro | Pro | Pro | Phe 270 | Ala | Pro |
| Pro | Val | Met 275 | Glu | Phe | Pro | Ala | Ala 280 | His | Asp | Arg | Met | Val 285 | Tyr | Leu | Gly |
| Leu | Ser 290 | Asp | Tyr | Phe | Phe | Asn 295 | Thr | Ala | Gly | Leu | Val 300 | Tyr | Gln | Glu | Ala |
| Gly 305 | Val | Leu | Lys | Met | Thr 310 | Leu | Arg | Asp | Asp | Met 315 | Ile | Pro | Lys | Glu | Ser 320 |
| Lys | Phe | Arg | Leu | Thr 325 | Thr | Lys | Phe | Phe | Gly 330 | Thr | Phe | Leu | Pro | Glu 335 | Val |
| Ala | Lys | Lys | Phe 340 | Pro | Asn | Met | Lys | Ile 345 | Gln | Ile | His | Val | Ser 350 | Ala | Ser |
| Thr | Pro | Pro 355 | His | Leu | Ser | Val | Gln 360 | Pro | Thr | Gly | Leu | Thr 365 | Phe | Tyr | Pro |
| Ala | Val 370 | Asp | Val | Gln | Ala | Phe 375 | Ala | Val | Leu | Pro | Asn 380 | Ser | Ser | Leu | Ala |
| Ser 385 | Leu | Phe | Leu | Ile | Gly 390 | Met | His | Thr | Thr | Gly 395 | Ser | Met | Glu | Val | Ser 400 |
| Ala | Glu | Ser | Asn | Arg 405 | Leu | Val | Gly | Glu | Leu 410 | Arg | Leu | Asp | Arg 415 | Leu | Leu |
| Leu | Gln | Leu | Lys 420 | His | Ser | Asn | Ile | Gly 425 | Pro | Phe | Pro | Val | Glu 430 | Leu | Leu |

```
Gln  Asp  Ile  Met  Asn  Tyr  Ile  Val  Pro  Ile  Leu  Val  Leu  Pro  Arg  Val
              435                      440                     445

Asn  Glu  Lys  Leu  Gln  Lys  Gly  Phe  Pro  Leu  Pro  Thr  Pro  Ala  Arg  Val
     450                     455                     460

Gln  Leu  Tyr  Asn  Val  Val  Leu  Gln  Pro  His  Gln  Asn  Phe  Leu  Leu  Phe
465                      470                     475                          480

Gly  Ala  Asp  Val  Val  Tyr  Lys
                    485
```

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Isolated native B/PI ( x i ) SEQUENCE DESCRIPTION: SEQ ID NO:5:

```
Val  Asn  Pro  Gly  Val  Val  Val  Arg  Ile  Ser  Gln  Lys  Gly  Leu  Asp  Tyr
1               5                        10                          15

Ala  Ser  Gln  Gln  Gly
               20
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Lys  Trp  Lys  Ala  Gln  Lys  Arg  Phe  Leu  Lys
1               5                        10
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Cys  Lys  Trp  Lys  Ala  Gln  Lys  Arg  Phe  Leu  Lys
1                    5                        10
```

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Lys  Trp  Lys  Ala  Gln  Lys  Arg  Phe  Leu  Lys  Met  Ser  Gly
1               5                        10
```

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Lys  Ile  Ser  Gly  Lys  Trp  Lys  Ala  Gln  Lys  Arg  Phe  Leu  Lys
 1              5                        10
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Cys  Lys  Ile  Ser  Gly  Lys  Trp  Lys  Ala  Gln  Lys  Arg  Phe  Leu  Lys
 1              5                        10                        15
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Glu  Phe  Tyr  Ser  Glu  Asn  His  His  Asn  Pro  Lys  Trp  Lys  Ala  Gln  Lys
 1              5                        10                        15

Arg  Phe  Leu  Lys
               20
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Cys  Glu  Phe  Tyr  Ser  Glu  Asn  His  His  Asn  Pro  Lys  Trp  Lys  Ala  Gln
 1              5                        10                        15

Lys  Arg  Phe  Leu  Lys
                    20
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Met  Arg  Glu  Asn  Met  Ala  Arg  Gly  Pro  Cys
 1              5                        10
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Lys  Glu  Leu  Lys  Arg  Ile  Lys  Ile  Pro  Asp  Tyr
 1                  5                        10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Lys  Leu  Gly  Ser  Asn  Pro  Thr  Ser  Gly  Lys
 1                  5                        10
```

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Lys  Lys  Ile  Glu  Ser  Ala  Leu  Arg  Asn  Lys  Met
 1                  5                        10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Cys  Glu  Phe  Tyr  Ser  Glu  Asn  His  His  Asn  Pro  Gly
 1                  5                        10
```

( 2 ) INFORMATION FOR SEQ ID NO:18:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Cys  Asn  Glu  Lys  Leu  Gln  Lys  Gly  Phe  Pro  Leu
 1                  5                        10
```

( 2 ) INFORMATION FOR SEQ ID NO:19:

( i ) SEQUENCE CHARACTERISTICS:
        ( A ) LENGTH: 19 amino acids (B) TYPE: amino acid
(D) TOPOLOGY: linear (ii) MOLECULE TYPE: peptide (xi) SEQUENCE DESCRIPTION: SEQ ID NO:19:

```
Lys Ile Ser Gly Lys Trp Lys Ala Gln Lys Arg Phe Leu Lys Met Ser
1               5                   10                  15
Gly Asn Phe
```

(2) INFORMATION FOR SEQ ID NO:20:

(i) SEQUENCE CHARACTERISTICS:
   (A) LENGTH: 27 amino acids
   (B) TYPE: amino acid
   (D) TOPOLOGY: linear (ii) MOLECULE TYPE: peptide (xi) SEQUENCE DESCRIPTION: SEQ ID NO:20:

```
Asn Ala Asn Ile Lys Ile Ser Gly Lys Trp Lys Ala Gln Lys Arg Phe
1               5                   10                  15
Leu Lys Met Ser Gly Asn Phe Asp Leu Ser Ile
            20                  25
```

(2) INFORMATION FOR SEQ ID NO:21:

(i) SEQUENCE CHARACTERISTICS:
   (A) LENGTH: 26 amino acids
   (B) TYPE: amino acid
   (D) TOPOLOGY: linear (ii) MOLECULE TYPE: peptide (xi) SEQUENCE DESCRIPTION: SEQ ID NO:21:

```
Val Asn Pro Gly Val Val Arg Ile Ser Gln Lys Gly Leu Asp Tyr
1               5                   10                  15
Ala Ser Gln Gln Gly Thr Ala Ala Leu Gln
            20                  25
```

(2) INFORMATION FOR SEQ ID NO:22:

(i) SEQUENCE CHARACTERISTICS:
   (A) LENGTH: 11 amino acids
   (B) TYPE: amino acid
   (D) TOPOLOGY: linear (ii) MOLECULE TYPE: peptide (xi) SEQUENCE DESCRIPTION: SEQ ID NO:22:

```
Glu Phe Tyr Ser Glu Asn His His Asn Pro Gly
1               5                   10
```

(2) INFORMATION FOR SEQ ID NO:23:

(i) SEQUENCE CHARACTERISTICS:
   (A) LENGTH: 10 amino acids
   (B) TYPE: amino acid
   (D) TOPOLOGY: linear (ii) MOLECULE TYPE: peptide (xi) SEQUENCE DESCRIPTION: SEQ ID NO:23:

```
Asn Glu Lys Leu Gln Lys Gly Phe Pro Leu
1               5                   10
```

(2) INFORMATION FOR SEQ ID NO:24:

( i ) SEQUENCE CHARACTERISTICS:
- ( A ) LENGTH: 10 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:24:

```
Lys Trp Lys Phe Lys Gln Arg Ala Leu Lys
1               5                   10
```

( 2 ) INFORMATION FOR SEQ ID NO:25:

( i ) SEQUENCE CHARACTERISTICS:
- ( A ) LENGTH: 12 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:25:

```
Cys Lys Trp Lys Ala Gln Lys Arg Phe Leu Lys Cys
1               5                   10
```

( 2 ) INFORMATION FOR SEQ ID NO:26:

( i ) SEQUENCE CHARACTERISTICS:
- ( A ) LENGTH: 11 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:26:

```
Lys Trp Lys Ala Gln Lys Arg Phe Leu Lys Cys
1               5                   10
```

( 2 ) INFORMATION FOR SEQ ID NO:27:

( i ) SEQUENCE CHARACTERISTICS:
- ( A ) LENGTH: 14 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:27:

```
Cys Lys Trp Lys Ala Gln Lys Arg Phe Leu Lys Met Ser Gly
1               5                   10
```

( 2 ) INFORMATION FOR SEQ ID NO:28:

( i ) SEQUENCE CHARACTERISTICS:
- ( A ) LENGTH: 29 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:28:

```
Cys Asn Ala Asn Ile Lys Ile Ser Gly Lys Trp Lys Ala Gln Lys Arg
1               5                   10                  15
Phe Leu Lys Met Ser Gly Asn Phe Asp Leu Ser Ile Cys
                20                  25
```

( 2 ) INFORMATION FOR SEQ ID NO:29:

( i ) SEQUENCE CHARACTERISTICS:

(A) LENGTH: 21 amino acids
(B) TYPE: amino acid
(D) TOPOLOGY: linear (ii) MOLECULE TYPE: peptide (xi) SEQUENCE DESCRIPTION: SEQ ID NO:29:

Cys Lys Ile Ser Gly Lys Trp Lys Ala Gln Lys Arg Phe Leu Lys Met
1               5                   10                  15
Ser Gly Asn Phe Cys
            20

(2) INFORMATION FOR SEQ ID NO:30:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:30:

Cys Glu Phe Tyr Ser Glu Asn His His Asn Pro
1               5                   10

(2) INFORMATION FOR SEQ ID NO:31:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (xi) SEQUENCE DESCRIPTION: SEQ ID NO:31:

Cys Val Asn Pro Gly Val Val Val Arg Ile Ser Gln Lys Gly Leu Asp
1               5                   10                  15
Tyr Ala Ser Gln Gln Gly Thr Ala Ala Leu Gln
            20                  25

(2) INFORMATION FOR SEQ ID NO:32:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:32:

Ser Asp Ser Phe Lys Ile Lys His Leu Gly Lys Gly His Tyr Ser Phe
1               5                   10                  15
Tyr Ser Met Asp Ile Arg Glu Phe Gln
            20                  25

(2) INFORMATION FOR SEQ ID NO:33:

(i) SEQUENCE CHARACTERISTICS:
    (A) LENGTH: 29 amino acids
    (B) TYPE: amino acid
    (D) TOPOLOGY: circular (ii) MOLECULE TYPE: peptide (xi) SEQUENCE DESCRIPTION: SEQ ID NO:33:

Cys Asn Ala Asn Ile Lys Ile Ser Gly Lys Trp Lys Ala Gln Lys Arg
1               5                   10                  15

```
        Phe Leu Lys Met Ser Gly Asn Phe Asp Leu Ser Ile Cys
                 20                  25
```

(2) INFORMATION FOR SEQ ID NO:34:

(i) SEQUENCE CHARACTERISTICS:
        (A) LENGTH: 21 amino acids
        (B) TYPE: amino acid
        (D) TOPOLOGY: circular (ii) MOLECULE TYPE: peptide (xi) SEQUENCE DESCRIPTION: SEQ ID NO:34:

```
Cys Lys Ile Ser Gly Lys Trp Lys Ala Gln Lys Arg Phe Leu Lys Met
1             5                   10                  15

Ser Gly Asn Phe Cys
             20
```

(2) INFORMATION FOR SEQ ID NO:35:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:35:

```
Trp Lys Lys Phe Lys Gln Arg Ala Leu Lys
1             5                   10
```

(2) INFORMATION FOR SEQ ID NO:36:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:36:

```
Lys Lys Lys Trp Phe Arg Leu Ala Lys Gln
1             5                   10
```

(2) INFORMATION FOR SEQ ID NO:37:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:37:

```
Lys Trp Lys Phe Lys Lys Arg Ala Leu Lys
1             5                   10
```

(2) INFORMATION FOR SEQ ID NO:38:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:38:

```
Lys Lys Lys Phe Phe Arg Leu Ala Lys Gln
1             5                   10
```

(2) INFORMATION FOR SEQ ID NO:39:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:39:

```
Lys Lys Lys Ala Phe Arg Leu Ala Lys Gln
1               5                   10
```

(2) INFORMATION FOR SEQ ID NO:40:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO:40:

```
Cys Lys Trp Lys Ala Gln Lys Arg Phe Leu Lys Cys
1               5                   10
```

(2) INFORMATION FOR SEQ ID NO:41:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:41:

```
Cys Lys Glu Leu Lys Arg Ile Lys Ile Pro Asp Tyr
1               5                   10
```

(2) INFORMATION FOR SEQ ID NO:42:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:42:

```
Cys Lys Lys Ile Glu Ser Ala Leu Arg Asn Lys Met
1               5                   10
```

(2) INFORMATION FOR SEQ ID NO:43:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:43:

```
Cys Lys Leu Gly Ser Asn Pro Thr Ser Gly Lys
1               5                   10
```

(2) INFORMATION FOR SEQ ID NO:44:

(i) SEQUENCE CHARACTERISTICS:

(A) LENGTH: 27 amino acids
(B) TYPE: amino acid
(D) TOPOLOGY: linear (ii) MOLECULE TYPE: peptide (xi) SEQUENCE DESCRIPTION: SEQ ID NO:44:

```
Leu Pro Ser Ser Gln Ile Ser Met Val Pro Asn Val Gly Leu Lys Phe
1               5                   10                  15
Ser Ile Ser Asn Ala Asn Ile Lys Ile Ser Gly
            20              25
```

(2) INFORMATION FOR SEQ ID NO:45:

(i) SEQUENCE CHARACTERISTICS:
(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO:45:

```
Met Ser Gly Asn Phe Asp Leu Ser Ile Glu Gly Met Ser Ile Ser Ala
1               5                   10                  15
Asp Leu
```

(2) INFORMATION FOR SEQ ID NO:46:

(i) SEQUENCE CHARACTERISTICS:
(A) LENGTH: 32 amino acids
(B) TYPE: amino acid
(D) TOPOLOGY: linear (ii) MOLECULE TYPE: peptide (xi) SEQUENCE DESCRIPTION: SEQ ID NO:46:

```
Pro Thr Ile Thr Cys Ser Ser Cys Ser Ser His Ile Asn Ser Val His
1               5                   10                  15
Val His Ile Ser Lys Ser Lys Val Gly Trp Leu Ile Gln Leu Phe His
            20              25                  30
```

(2) INFORMATION FOR SEQ ID NO:47:

(i) SEQUENCE CHARACTERISTICS:
(A) LENGTH: 30 amino acids
(B) TYPE: amino acid
(D) TOPOLOGY: linear (ii) MOLECULE TYPE: peptide (xi) SEQUENCE DESCRIPTION: SEQ ID NO:47:

```
Met Asn Ser Gln Val Cys Glu Lys Val Thr Asn Ser Val Ser Ser Lys
1               5                   10                  15
Leu Gln Pro Tyr Phe Gln Thr Leu Pro Val Met Thr Lys Ile
            20              25                  30
```

(2) INFORMATION FOR SEQ ID NO:48:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:48:

```
Ile Lys Thr Lys Lys Phe Leu Lys Lys Thr
```

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

```
Lys  Thr  Lys  Cys  Lys  Phe  Leu  Lys  Lys  Cys
1                  5                        10
```

( 2 ) INFORMATION FOR SEQ ID NO:50:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:50:

```
Cys  Lys  Thr  Lys  Cys  Lys  Phe  Leu  Lys  Lys  Cys
1                  5                        10
```

( 2 ) INFORMATION FOR SEQ ID NO:51:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:

```
Met  Ser  Gly  Asn  Phe  Asp  Leu  Ser  Ile  Glu
1                  5                        10
```

( 2 ) INFORMATION FOR SEQ ID NO:52:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:52:

```
Ile  Ser  Asn  Ala  Asn  Ile  Lys  Ile  Ser  Gly
1                  5                        10
```

( 2 ) INFORMATION FOR SEQ ID NO:53:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:53:

```
Ala  Asn  Ile  Lys  Ile  Ser  Gly  Lys  Trp  Lys
1                  5                        10
```

( 2 ) INFORMATION FOR SEQ ID NO:54:

( i ) SEQUENCE CHARACTERISTICS:
 ( A ) LENGTH: 10 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:54:

Lys Ile Ser Gly Lys Trp Lys Ala Gln Lys
1               5                   10

( 2 ) INFORMATION FOR SEQ ID NO:55:

( i ) SEQUENCE CHARACTERISTICS:
 ( A ) LENGTH: 10 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:55:

Gln Lys Arg Phe Leu Lys Met Ser Gly Asn
1               5                   10

( 2 ) INFORMATION FOR SEQ ID NO:56:

( i ) SEQUENCE CHARACTERISTICS:
 ( A ) LENGTH: 10 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:56:

Phe Leu Lys Met Ser Gly Asn Phe Asp Leu
1               5                   10

( 2 ) INFORMATION FOR SEQ ID NO:57:

( i ) SEQUENCE CHARACTERISTICS:
 ( A ) LENGTH: 12 amino acids
 ( B ) TYPE: amino acid
 ( D ) TOPOLOGY: circular ( i i ) MOLECULE TYPE: peptide ( x i ) SEQUENCE DESCRIPTION: SEQ ID NO:57:

Cys Phe Leu Lys Met Ser Gly Asn Phe Asp Leu Cys
1               5                   10

( 2 ) INFORMATION FOR SEQ ID NO:58:

( i ) SEQUENCE CHARACTERISTICS:
 ( A ) LENGTH: 11 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:58:

Asn Ala Asn Ile Lys Ile Ser Gly Lys Trp Lys
1               5                   10

( 2 ) INFORMATION FOR SEQ ID NO:59:

( i ) SEQUENCE CHARACTERISTICS:
 ( A ) LENGTH: 22 amino acids
 ( B ) TYPE: amino acid
 ( D ) TOPOLOGY: linear (i) MOLECULE TYPE: peptide (xi) SEQUENCE DESCRIPTION: SEQ ID NO:59:

Cys Glu Phe Tyr Ser Glu Asn His His Asn Pro Lys Trp Lys Ala Gln
1               5                   10                  15

Lys Arg Phe Leu Lys Cys
              20

(2) INFORMATION FOR SEQ ID NO:60:

(i) SEQUENCE CHARACTERISTICS:
   (A) LENGTH: 16 amino acids
   (B) TYPE: amino acid
   (D) TOPOLOGY: linear (ii) MOLECULE TYPE: peptide (xi) SEQUENCE DESCRIPTION: SEQ ID NO:60:

Cys Lys Ile Ser Gly Lys Trp Lys Ala Gln Lys Arg Phe Leu Lys Cys
1               5                   10                  15

What is claimed is:

1. A bactericidal peptide having about 10 to 100 amino acids, wherein said peptide is bactericidal for Pseudomonas species and comprises the amino acid sequence KWKAQKRFLK (SEQ ID NO:6).

2. A bactericidal peptide according to claim 1, selected from the group consisting of:
KWKAQKRFLK (SEQ ID NO:6),
CKWKAQKRFLK (SEQ ID NO:7),
CKWKAQKRFLKC (SEQ ID NO:28),
EFYSENHHNPKWKAQKRFLK (SEQ ID NO:11),
CEFYSENHHNPKWKAQKRFLK (SEQ ID NO:12),
KISGKWKAQKRFLKMSGNF (SEQ ID NO:20),
CKISGKWKAQKRFLKMSGNFC (SEQ ID NO:29),
NANIKISGKWKAQKRFLKMSGNFDLSI (SEQ ID NO:20), and
CNANIKISGKWKAQKRFLKMSGNFDLSIC (SEQ ID NQ:28).

3. A peptide according to claim 1, wherein the peptide is a dimer.

4. A peptide according to claim 1 further comprising a carrier protein, wherein the peptide is covalently attached to the carrier protein.

5. A peptide according to claim 1, wherein said peptide is bactericidal for P. aeruginosa at about $10^{-7}$ to about $10^{-9}$M and has a sequence:
NANIKISGKWKAQKRFLKMSGNFDLSI (SEQ ID NO:20), or
CNANIKISGKWKAQKRFLKMSGNFDLSIC (C#82-108C) (SEQ ID NO:28), and wherein the peptide is in linear or cyclic form.

6. A peptide according to claim 1, wherein the peptide has about 10 to 40 amino acids.

7. A peptide with endotoxin neutralizing activity and which has a sequence selected from the group consisting of:
VNPGVVVRISQKGLDYASQQGTAALQ (1-26) (SEQ ID NO:21),
KKIESALRNKM (160-170) (SEQ ID NO:16),
CEFYSENHHNP (C227-236) (SEQ ID NO: 17),
CNEKLQKGFPL (C418-427) (SEQ ID NO:18),
NANIKISGKWKAQKRFLKMSGNFDLSI (82-108) (SEQ ID NO:20),
CNANIKISGKWKAQKRFLKMSGNFDLSIC (C82-108c) (SEQ ID NO:28),
CKWKAQKRFLKC (C90-99C) (SEQ ID NO: 25),
CKISGKWKAQKRFLKMSGNFC (C86-104C) (SEQ ID NO:29), and
SDSFIKHLGKGHYSFYSMDIREFQ (SEQ ID NO:32).

8. A peptide, with both endotoxin neutralizing activity and bactericidal activity for P. aeruginosa, wherein the peptide has an amino acid sequence selected from the group consisting of:
EFYSENHHNPKWKAQKRFLK (SEQ ID NO:11),
CKISGKWKAQKRFLKMSGNFC (SEQ ID NO:29),
CEFYSENHHNPKWKAQKRFLKC (chybrid) (SEQ ID NO:12),
CKISGKWKAQKRFLK (SEQ ID NO:10),
CKISGKWKAQKRFLK (dimer C86-99) (SEQ ID NO:10),
NANIKISGKWKAQKRFLKMSGNFDLSI (82-108) (SEQ ID NO:20), and
CNANIKISGKWKAQKRFLKMSGNFDLSIC (C82-108C) (SEQ ID NO:28).

9. A hybrid peptide with endotoxin neutralizing activity and bactericidal activity; wherein said peptide has at least one amino acid sequence of a peptide having endotoxin neutralizing activity combined with at least one different amino acid sequence of a peptide that has bactericidal activity.

10. A hybrid peptide according to claim 9, wherein the amino acid sequence of the endotoxin neutralizing peptide is selected from the group consisting of:
CEFYSENHHNP (C227-236) (SEQ ID NO:17),
VNPGVVVRISQKGLDYASQQGTAALQ (1-26) (SEQ ID NO:21), and
CVNPGVVVRISQKGLDYASQQGTAALQ (C1-26) (SEQ ID NO:31).

11. A hybrid peptide according to claim 9, wherein the amino acid sequence of the bactericidal peptide is selected from the group consisting of:
NANIKISGKWKAQKRFLKMSGNFDLSI (82-108) (SEQ ID NO:20),
CNANIKISGKWKAQKRFLKMSGNFDLSIC (C82-108C) (SEQ ID NO:28),

KWKAQKRFLK (90-99) (SEQ ID NO:6),

CKWKAQKRFLKC (C90-99C) (SEQ ID NO:25),

KISGKWKAQKRFLKMSGNF (86-104C) (SEQ ID NO:19), and

CKISGKWKAQKRFLKMSGNFC (C86-104) (SEQ ID NO:29).

12. A prosthetic device having an amount of bactericidal peptide attached to a surface of the prosthetic device effective to inhibit the growth of bacteria on the surface wherein the peptide is bactericidal for Pseudomonas species and has about 10 to 100 amino acids and comprises the amino acid sequence KWKAQKRFLK (SEQ ID NO:6).

13. A method of treating a bacterial infection comprising administering an amount of pharmaceutical composition effective to inhibit the bacterial infection to an animal, wherein said pharmaceutical composition comprises:

(a) a bactericidal peptide for Pseudomonas species having about 10 to 100 amino acids or pharmaceutically acceptable salts thereof comprising an amino acid sequence KWKAQKRFLK (SEQ ID NO:6) in admixture with (b) a pharmaceutically acceptable carrier.

14. A method according to claim 13, wherein the bacteria is selected from the group consisting of *P. aeruginosa, P. cepacia,* and *E. coli* B.

15. A method according to claim 13, wherein the bactericidal peptide has an amino acid sequence selected from the group consisting of:

KWKAQKRFLK (SEQ ID NO:6),

CKWKAQKRFLKC (C90-99C) (SEQ ID NO:25),

NANIKISGKWKAQKRFLKMSGNFDLSI (82-108) (SEQ ID NO:20),

CNANIKISGKWKAQKRFLKMSGNFDLSIC (C82-108C) (SEQ ID NO:28),

KISGKWKAQKRFLKMSGNF (SEQ ID NO:19), and

CKISGKWKAQKRFLKMSGNFC (SEQ ID NO:29), and wherein said peptide is in cyclic or linear form.

16. A method according to claim 13, wherein the bacteria is *S. aureus.*

17. A method according to claim 13 further comprising administering a second pharmaceutical composition to the animal, wherein the second pharmaceutical composition can inhibit the bacterial infection.

18. A method of treating endotoxin shock comprising:

administering an amount of a pharmaceutical composition effective to diminish the symptoms of endotoxin shock to an animal, wherein the pharmaceutical composition comprises:

(a) a bactericidal peptide for Pseudomonas species having about 10 to 100 amino acids or pharmaceutically acceptable salts thereof comprising an amino acid sequence KWKAOKRFLK (SEQ ID NO:6) in admixture with (b) a pharmaceutically acceptable carrier.

19. A bactericidal peptide, wherein said peptide is bactericidal for Pseudomonas species and comprises an amino acid sequence KWKAQKRFLK (SEQ ID NO:6) and wherein the peptide has at least about a 12 amino acid cyclic peptide or cyclic portion of the peptide and wherein the amino acid sequence KWKAQKRFLK (SEQ ID NO:6) is present in the cyclic peptide or the cyclic portion of the peptide.

20. A bactericidal peptide, wherein said peptide is bactericidal for Pseudomonas species and comprises the amino acid sequence KWKAQKRFLK (SEQ ID NO:6) and wherein the peptide has a terminal amino acid selected from the group consisting of N-terminal cystein, C-terminal cysteine, and N-terminal and C-terminal cysteines.

21. A bactericidal peptide, wherein said peptide is bactericidal for Pseudomonas species and comprises an amino acid sequence KWKAQKRFLK (SEQ ID NO:6) wherein the peptide has at least two cysteine residues located so that a cyclic portion of the peptide can be formed, wherein the cyclic portion of the peptide that can be formed comprises the amino acid sequence KWKAQKRFLK (SEQ ID NO:6).

22. A bactericidal peptide according to claim 20 wherein the peptide has an amino acid sequence selected from the group consisting of:

CKWKAQKRFLK (SEQ ID NO:7),

CEFYSENHHNPKWKAQKRFLK (SEQ ID NO:12),

CKWKAQKRFLKC (SEQ ID NO:25),

KWKAQKRFLKC (SEQ ID NO:26),

CKISGKWKAQKRFLKMSGNFC (SEQ ID NO:29), and

CNANIKISGKWKAQKRFLKMSGNFDLSIC (SEQ ID NO:28).

23. A peptide according to claim 19 wherein the peptide has a sequence selected from the group consisting of:

CKWKAQKRFLKC (SEQ ID NO:25),

CNANIKISGKWKAQKRFLKMSGNFDLSIC (SEQ ID NO:28), and

CKISGKWKAQKRFLKMSGNFC (SEQ ID NO:29).

24. A method of treating a bacterial infection comprising administering an amount of a pharmaceutical composition effective to inhibit the bacterial infection to an animal, wherein such pharmaceutical composition comprises (a) a peptide according to claim 19 or pharmaceutically acceptable salts thereof in a mixture with (b) a pharmaceutically acceptable carrier.

25. A method of treating a bacterial infection comprising administering an amount of pharmaceutical composition effective to inhibit the bacterial infection to an animal wherein said pharmaceutical composition comprises (a) a peptide according to claim 21 or pharmaceutically acceptable salts thereof in a mixture with (b) a pharmaceutically acceptable carrier.

26. A prosthetic device having an amount of bactericidal peptide attached to a surface of the prosthetic device effective to inhibit the growth of bacterial on the surface, wherein the peptide is bactericidal for a Pseudomonas species and comprises the amino acid sequence KWKAQKRFLK (SEQ ID NO6) and wherein the peptide has at least about a 12 amino acid cyclic peptide or cyclic portion of the peptide and wherein the amino acid sequence KWKAQKRFLK (SEQ ID NO:6) is present in the cyclic peptide or the cyclic portion of the peptide.

27. A prosthetic device having an amount of bactericidal peptide attached to a surface of the prosthetic device effective to inhibit the growth of bacteria on the surface, wherein the peptide is bactericidal for a Pseudomonas species and comprises the amino acid sequence KWKAQKRFLK (SEQ ID NO:6) and wherein the peptide has at least two cysteine residues located so that a cyclic portion of the peptide can be formed wherein the cyclic portion of the peptide that can be formed comprises the amino acid sequence KWKAQKRFLK (SEQ ID NO:6).

* * * * *

UNITED STATES PATENT AND TRADEMARK OFFICE
CERTIFICATE OF CORRECTION

PATENT NO. : 5,786,324

DATED : JULY 28, 1998

INVENTOR(S) : GRAY ET AL.

It is certified that error appears in the above-identified patent and that said Letters Patent is hereby corrected as shown below:

Col. 4, line 48: "Fig. 4A" should read —Fig. 4, 4A—

Col. 5, line 56: "1 x 10−9M" should read —1 x $10^{-9}$M—

Col. 5, line 60: "$10^{-1}$M" should read —$10^{-10}$M—

Col. 16, line 20: "TNFA" should read —TNFα—

Col. 22, line 36: "3x10−5M" should read —3x$10^{-5}$M—

Col. 22, line 54: "3.0 x $10^{-6}$M" should read —3.0 x $10^{-5}$M—

Col. 27, line 37: "1.5 x $10^6$M   3.0 x $10^4$M" should read —1.5 x $10^{-6}$M   3.0 x $10^{-4}$M—

Col. 27, line 38: "1.5 x $10^5$M   7.5 x $10^5$M" should read —1.5 x $10^{-5}$M   7.5 x $10^{-5}$M—

Col. 27, line 39: "3.0 x $10^6$M   1.2 x $10^4$M" should read —3.0 x $10^{-6}$M   1.2 x $10^{-4}$M—

Col. 27, line 40: "3.0 x $10^5$M   3.0 x $10^4$M" should read —3.0 x $10^{-5}$M   3.0 x $10^{-4}$M—

Col. 27, line 41: "1.5 x $10^6$M   4.5 x $10^4$M" should read —1.5 x $10^{-6}$M   4.5 x $10^{-4}$M—

Col. 27, line 42: "6.0 x $10^8$M   2.0 x $10^5$M" should read —6.0 x $10^{-8}$M   2.0 x $10^{-5}$M—

UNITED STATES PATENT AND TRADEMARK OFFICE
CERTIFICATE OF CORRECTION

PATENT NO. : 5,786,324

DATED : JULY 28, 1998

INVENTOR(S) : GRAY ET AL.

It is certified that error appears in the above-identified patent and that said Letters Patent is hereby corrected as shown below:

Col. 27, line 43: "$3.0 \times 10^7 M \quad 3.0 \times 10^5 M$" should read —$3.0 \times 10^{-7} M \quad 3.0 \times 10^{-5} M$—

Col. 27, line 44: "$1.5 \times 10^5 M \quad 4.5 \times 10^4 M$" should read —$1.5 \times 10^{-5} M \quad 4.5 \times 10^{-4} M$—

Col. 27, line 45: "$1.0 \times 10^5 M \quad 3.0 \times 10^4 M$" should read —$1.0 \times 10^{-5} M \quad 3.0 \times 10^{-4} M$—

Col. 27, line 46: "$1.5 \times 10^7 M \quad 4.5 \times 10^4 M$" should read —$1.5 \times 10^{-7} M \quad 4.5 \times 10^{-4} M$—

Col. 27, line 47: "$1.2 \times 10^4 M \quad 7.5 \times 10^5 M$" should read —$1.2 \times 10^{-4} M \quad 7.5 \times 10^{-5} M$—

Col. 27, line 48: "$1.5 \times 10^7 M \quad 2.25 \times 10^4 M$" should read —$1.5 \times 10^{-7} M \quad 2.25 \times 10^{-4} M$—

Signed and Sealed this

Eighteenth Day of April, 2000

*Attest:*

Q. TODD DICKINSON

*Attesting Officer*         *Director of Patents and Trademarks*